(12) United States Patent
Shimkets

(10) Patent No.: US 6,486,299 B1
(45) Date of Patent: Nov. 26, 2002

(54) GENES AND PROTEINS PREDICTIVE AND THERAPEUTIC FOR STROKE, HYPERTENSION, DIABETES AND OBESITY

(75) Inventor: Richard A. Shimkets, West Haven, CT (US)

(73) Assignee: CuraGen Corporation, New Haven, CT (US)

( * ) Notice: Subject to any disclaimer, the term of this patent is extended or adjusted under 35 U.S.C. 154(b) by 0 days.

(21) Appl. No.: 09/161,939

(22) Filed: Sep. 28, 1998

(51) Int. Cl.⁷ .......................... C07K 1/00; A61K 35/14
(52) U.S. Cl. .................... 530/350; 530/380; 530/800
(58) Field of Search ............................. 435/183, 6, 8; 424/94.5, 139.1; 514/44; 530/350, 380, 800

(56) References Cited

FOREIGN PATENT DOCUMENTS

| WO | WO 90/11364 | | 10/1990 |
|---|---|---|---|
| WO | WO 921049 A | * | 1/1992 |
| WO | WO 97/15690 | | 5/1997 |

OTHER PUBLICATIONS

GenBank Accession No. Q08857, Feb. 1, 1995, Endemann et al.*
GenBank Accession No. I49590, Endemann et al. Jul. 2, 1996.*
GenBank AccessionNo. Q07969, Abumrad et al. Feb. 1, 1995.*
Ahn HS, Bercovici A, Boykow G, et al. Potent tetracylic guanine inhibitors of PDE1 and PDE5 cyclic guanosine monophosphate phosphodiesterases with oral antihypertensive activity. *J Med Chem* 1997; 40:2196–210.
Aitman TJ, Gotoda T, Evans AL, et al. Quantitative trait loci for cellular defects in glucose and fatty acid metabolism in hypertensive rats. *Nat Genet* 1997; 16:197–201.
Amerini S, Mantelli L, Filippi S, Ledda F. Age–dependent modifications of the role of prostanoids in cardiac preparations from normotensive and hypertensive rats. *Pharmacol Res* 1993; 28:341–50.
Ando K, Ono A, Sato Y, Fujita T. Involvement of prostaglandins and renal haemodynamics in salt–sensitivity of young spontaneously hypertensive rats. *J Hypertens* 1993; 11:373–7.
Armario A, Gavalda A, Marti J. Comparison of the behavioural and endocrine response to forced swimming stress in five inbred strains of rats. *Psychoneuroendocrinology* 1995; 20:879–90.
Asano H, Shimizu K, Muramatsu M, et al. Prostaglandin H2 as an endothelium–derived contracting factor modulates endothelin–1–induced contraction. *J. Hypertens* 1994; 12:383–90.

Basu AK, Ghosh S, Mohanty PK, Watlington CO. Augmented arterial pressure responses to cyclosporine in spontaneously hypertensive rats. Role of cytochrome P–450 3A. *Hypertension* 1994; 24:480–5.
Benter IF, Ferrario CM, Morris M, Diz Dl. Antihypertensive actions of angiotensin–(1–7) in spontaneously hypertensive rats. *Am J Physiol* 1995; 269:H31 3–9.
Bohmann O, Schaible U, Schollmeyer P, Rump LC. Alpha 2D–adrenoceptors modulate renal noradrenaline release in normotensive and spontaneously hypertensive rats. *Eur J Pharmacol* 1994; 271:283–92.
Bohmann O, Rump LC, Schaible U, von Kugelgen I. Alpha–adrenoceptor modulation of norepinephrine and ATP release in isolated kidneys of spontaneously hypertensive rats. *Hypertension* 1995:25:1224–31.
Boston PC, Hodgson WC. Changed in reactivity towards 5–hydroxytryptamine in the renal vasculature of the diabetic spontaneously hypertensive rat. *J Hypertens* 1997; 15:769–74.
Bottger A, van Lith HA, Kren V, et al. Quantitative trait loci influencing cholesterol and phospholipid phenotypes map to chromosomes that contain genes regulating blood pressure in the spontaneously hypertensive rat. *J Clin Invest* 1996; 98:856–62.
Braun C, Lang C, Hocher B, Gretz N, van der Woude FJ, Rohmeiss P. Influence of the renal endothelin system on the autoregulation of renal blood flow in spontaneously hypertensive rats. *Kidney Blood Press Res* 1997; 20:6–10.

(List continued on next page.)

Primary Examiner—Rebecca E. Prouty
Assistant Examiner—Manjunath N. Rao
(74) Attorney, Agent, or Firm—Mintz, Levin, Cohn, Ferris, Glovsky and Popeo, P.C.; Ivor R. Elrifi, Esq.; David E. Johnson, Esq.

(57) ABSTRACT

Common human diseases like diabetes and hypertension have been demonstrated to possess an associated genetic component composed of numerous underlying genetic defects. Traditional positional cloning of genes which possess the mutations responsible for complex disease has been hindered by both the low statistical power each locus may afford, and by the technically-laborious nature of the positional cloning methodologies. Disclosed herein is a methodology for the rapid identification of the genes responsible for quantitative trait loci (QTL) comprised of comprehensive gene expression analysis in organs relevant to disease in combination with the positional mapping of known QTL, so as to quantitatively identify candidate genes. This aforementioned methodology was applied to a total of five tissues/organs derived from the spontaneously hypertensive rat (SHR), the stroke-prone variant of the SHR (SHR-SP) and control Wistar Kyoto rats (WKY). Collectively these animals vary genetically in their predisposition to stroke, insulin sensitivity, blood pressure and body weight. These traits segregate into more than a dozen identified. The present invention discloses the differential-expression of sixty genes by GeneCalling® within five different tissues/organs among these animals. Additionally, five of the sixty genes were demonstrated to be localized within chromosomal regions linked to these traits of interest and possess amino acid substitutions which may contribute to the phenotype.

3 Claims, 7 Drawing Sheets

OTHER PUBLICATIONS

Cappelli–Bigazzi M, S. R, C. B, et al. Effects of high–cholesterol and atherogenic diets on vascular relaxation in spontaneously hypertensive rats. *Am J Physiol* 1997; 273:H647–54.

Cechetto DF, Kline RL. Effect of rilmenidine on arterial pressure and urinary output in the spontaneously hypertensive rat. *Eur J Pharmacol* 1997; 325:47–55.

Chaouloff F, Berton O, Aquerre S, Hay M, Mormede P. Effects of food deprivation on midbrain 5–HT1A autoreceptors in Lewis and SHR rats. *Neuropharmacology* 1997; 36:483–8.

Chatziantoniou C, Ruan X, Arendshorst WJ. Interactions of cAMP–mediated vasodilators with angiotensin II in rat kidney during hypertension. *Am J Physiol* 1993; 265:F845–52.

Chatziantoniou C, Adrendshorst WJ. Vascular interactions of prostaglandins with thromboxane in kidneys of rats developing hypertension. *Am J Physiol* 1993; 265:F250–6.

Clark JS, Jeffs B, Davidson AO, et al. Quantitative trait loci in genetically hypertensive rats. Possible sex specificity. *Hypertension* 1996;28:898–906.

Conyers RB, Werstiuk ES, Lee RM. Expression of functional beta–adrenoceptors and polyploidy development in cultured vascular smooth muscle cells from spontaneously hypertensive rats. *Can J Physiol Pharmacol* 1997; 75:375–82.

Dukacz SA, Adams MA, Kline RL. The persistent effect of long–term enalapril on pressure natriuresisin spontaneously hypertensive rats. *Am J Physiol* 1997; 273:F1 04–1 2.

Ecelbarger CA, Terris J, Frindt G, et al. Aquaporin–3 water channel localization and regulation in rat kidney. *Am J Physiol* 1995; 269:F663–72.

Eisner GM, Asico LD, Albrecht FE, Jose PA. Dopamine and dittiazem–induced natriuresis in the spontaneously hypertensive rat. *Am J Physiol* 1997; 273:R317–23.

Evans SJ, Jones JV, Levi AJ. Reduction in external K causes increased action potential shortening in ventricular myocytes from the spontaneously hypertensive rat. *J Hypertens* 1997; 15:659–66.

Failli P, Ruocco C, Fazzini A, Giotti A. Calcium waves in unstimulated left ventricular cardiomyocytes isolated from aged spontaneously hypertensive and normotensive rats. *Biochem Biophys Res Commun* 1997; 237:103–6.

Feng JJ, Arendshorst WJ. Enhanced renal vasoconstriction induced by vasopressin in SHR is mediated by V1 receptors. *Am J Physiol* 1996; 271:F304–13.

Gattu M, Wei J, Pauly JR, Urbanawiz S, Buccafusco JJ. Increased expression of M2 muscarinic receptor mRNA and binding sites in the rostral ventrolateral medulla of spontaneously hypertensive rats. *Brain Res* 1997; 756: 125–32.

Ghosh S, Grogan WM, Basu A, Watlington C. Renal corticosterone 6 beta–hydroxylase in the spontaneously hypertensive rat. *Biochim Biophys Acta* 1993; 1182:152–6.

Ghosh S, Palmer SM, Rodrigues NR, et al. Polygenic control of autoimmune diabetes in nonobese diabetic mice. *Nat Genet* 1993; 4:404–9.

Ghosh SS, Basu AK, Ghosh S, et al. Renal and hepatic family 3A cytochromes P450 (CYP3A) in spontaneously hypertensive rats. *Biochem Pharmacol* 1995; 50:49–54.

Gomez F, Lahmame A, de Kloet ER, Armario A. Hypothalamic–pituitary–adrenal response to chronic stress in five inbred rat strains: differential responses are mainly located at the adrenocortical level. *Neuroendocrinology* 1996; 63:327–37.

Guillaume P, Gutkowska J, Gianoulakis C. Alterations in brain levels of atrial and C–type natriuretic peptides after chronic moderate ethanol consumption in spontaneously hypertensive rats. *Eur J Pharmacol* 1997; 319:215–24.

Hamet P, Pausova Z, Dumas P, et al. Newborn and adult recombinant inbred strains: a tool to search for genetic determinants of target organ damage in hypertension. *Kidney Int* 1998; 53:1488–92.

Herman EH, Zhang J, Hasinoff BB, Chadwick DP, Clark JR, Jr., Ferrans VJ. Comparison of the protective effects against chronic dexornbioin cardiotoxicity and the rates of iron (III) displacement reactions of ICRF–187 and other bisdiketopiperazines. *Cancer Chemother Pharmacol* 1997; 40:400–8.

Hermans JJ, Steckel B, Thijssen HH, Janssen BJ, Netter KJ, Maser E. Comparison of 11 beta–hydroxysteroid dehydrogenase in spontaneously hypertensive and Wistar–Kyoto rats. *Steroids* 1995; 60:773–9.

Hilbert P, et al. Chromosomal mapping of two genetic loci associated with blood–pressure regulation in hereditary hypertensive rats [see comments]. *Nature* 1991; 353:521–9.

Hoyer J, Kohler R, Distler A. Mechanosensitive cation channels in aortic endothelium of normotensive and hypertensive rats. *Hypertension* 1997; 30:112–9.

Huang A, Sun D, Koller A. Endothelial dysfunction augments myogenic arteriolar constriction in hypertension. *Hypertension* 1993; 22:913–21.

Ikeda T, Gomi T, Sasaki Y. Effects of swim training on blood pressure, catecholamines and prostaglandins in spontaneously hypertensive rats. *Jpn Heart J* 1994; 35:205–11.

Ikenaga H, Suzuki H, Ishii N, Itoh H, Saruta T. Role of NO on pressure–natriuresis in Wistar–Kyoto and spontaneously hypertensive rats. *Kidney Int* 1993; 43:205–11.

Irvine RJ, White JM. The effects of central and peripheral angiotensin on hypertension and nociception in rats. *Pharmacol Biochem Behav* 1997; 57:37–41.

Jandeleit–Dahm K, Burrell LM, Johnston Cl, Koch KM. Elevated vascular angiotensin converting enzyme mediates increased neointima formation after balloon injury in spontaneously hypertensive rats. *J Hypertens* 1997; 15:643–50.

Jeffs B, Clark JS, Anderson NH, et al. Sensitivity to cerebral ischaemic insult in a rat model of stroke is determined by a single genetic locus. *Nat Genet* 1997; 16:364–7.

Kirchengast M. Preclinical considerations and results with the combination of verapamil and trandolapril: blood pressure reduction and beyond. *J Hypertens Suppl* 1997; 15:527–33.

Ko FN. Low–affinity thromboxane receptor mediates proliferation in cultured vascular smooth muscle cells of rats. *Arterioscler Thromb Vasc Biol* 1997; 17:1274–82.

Kohzuki M, Yasujima M, Kanazawa M, et al. Antihypertensive and renal–protective effects of losartan in streptozotocin diabetic rats. *J Hypertens* 1995; 13:97–103.

Kovacs P, Voigt B, Kloting I. Novel quantitative trait loci for blood pressure and related traits on rat chromosomes 1, 10, and 18. *Biochem Biophys Res Commun* 1997; 235:343–8.

Kreutz R, Hubner N, James MR, et al. Dissection of a quantitative trait locus for genetic hypertension on rat chromosome 10. *Proc Natl Acad Sci U S A* 1995; 92:8778–82.

Laurant P, Touyz RM, Schiffrin EL. Effect of magnesium on vascular tone and reactivity in pressurized mesenteric resistance arteries from spontaneously hypertensive rats. *Can J Physiol Pharmacol* 1997; 75:293–300.

Le Marquer–Domagala F, Finet M. Comparison of the nitric oxide and cyclo–oxygenase pathway in mesenteric resistance vessels of normotensive and spontaneously hypertensive rats. *Br J Pharmacol* 1997; 121:588–94.

Liu X, Songu–Mize E. Alterations in alpha subunit expression of cardiac Na+, K+–ATPase in spontaneously hypertensive rats: effect of antihypertensive therapy. *Eur J Pharmacol* 1997; 327:151–6.

Marti J, Armario A. Forced swimming behavior is not related to the corticosterone levels achieved in the test: a study with four inbred rat strains. *Physiol Behav* 1996; 59:369–73.

Mervaala EM, Malmberg L, Teravainen TL, et al. Influence of different dietary salts on the cardiovascular and renal effects of moxonidine in spontaneously hypertensive rats. *Naunyn Schmiedebergs Arch Pharmacol* 1997; 356:107–14.

Mervaala EM, et al. Cardiovascular effects of a low–dose combination of ramipril and felodipine in spontaneously hypertensive rats. *Br J Pharmacol* 1997; 121:503–10.

Mu JY, et al. The effects of enalapril on the natriuretic response evoked by an oral sodium load in sodium deprived normotensive and hypertensive rats. *Acta Physiol Scand* 1997; 160:157–64.

Nakagawara M, Kubota M, Atobe M, Kariya T. Strain difference in behavioral response to a new environment in rats. *Psychiatry Clin Neurosci* 1997; 51:167–70.

Narce M, Frenoux JM, Dardel V, et al. Fatty acid metabolism, pharmacological nutrients and hypertension. *Biochimie* 1997; 79: 135–8.

Nielsen S, et al. Congestive heart failure in rats is associated with increased expression and targeting of aquaporin–2 water channel in collecting dirt. *Proc Natl Acad Sci U S A* 1997; 94:5450–5.

Okuda M, Saito H, Urakami Y, Takano M, lnui K. cDNA cloning and functional expression of a novel rat kidney organic cation transporter, OCT2. *Biochem Biophys Res Commun* 1996; 224:500–7.

Oosting J, Struijker–Boudier HA, Janssen BJ. Circadian and ultradian control of cardiac output in spontaneous hypertension in rats. *Am J Physiol* 1997; 273:H66–75.

Oosting J, et al. Autonomic control of ultradian and circadian rhythms of blood pressure, heart rate, and baroreflex sensitivity in spontaneously hypertensive rats. *J Hypertens* 1997; 15:401–10.

Panarelli M, et al. Differences in temperature–sensitive receptor binding of glucocorticoids in spontaneously hypertensive and normotensive Wistar– Kyoto rats. *Steroids* 1995; 60:73–5.

Panzacchi G, Pieruzzi F, Castoldi G, et al. Effects of erythropoietin adminstration on blood pressure and urinary albumin excretion in rats. *Am J Hypertens* 1997; 10:772–8.

Patschan O, Kuttler B, Heemann U, Uber A, Rettig R. Kidneys from normotensive donors lower blood pressure in young transplanted spontaneously hypertensive rats. *Am J Physiol* 1997; 273:R175–80.

Perez–Alvarez V, Morales–Rios MS, Hong E, Joseph–Nathan P. Synthesis of 3–amino–2–(3–indolyl)propanol and propanoate derivatives and preliminary cardiovascular evaluation in rats. *J Pharm Pharmacol* 1997; 49:246–52.

Pinto YM, Buikema H, van Gilst WH, et al. Cardiovascular end–organ damage in Ren–2 transgenic rats compared to spontaneously hypertensive rats. *J Mol Med* 1997; 75:371–7.

Pompei P, et al. Regulation of preprotachykinin–A mRNA in genetic hypertensive and normotensive rats. *Brain Res Mol Brain Res* 1997; 47:78–86.

Porteri E, et al. Structural changes of small resistance arteries in spontaneously hypertensive rats after treatment with various doses of lacidipine. *J Hypertens* 1997; 15:619–25.

Poulat P, et al. Receptor and mechanism that mediate endothelin– and big endothelin–1– induced phosphoinositide hydrolysis in the rat spinal cord. *Eur J Pharmacol* 1996; 31 5:327–34.

Pravenec M, et al. Mapping of quantitative trait loci for blood pressure and cardiac mass in the rat by genome scanning of recombinant inbred strains. *J Clin Invest* 1995; 96:1973–8.

Preuss HG, Memon S, Dadgar A, Gongwei J. Effects of high sugar diets on renal fluid, electrolyte and mineral handling in rats: relationship to blood pressure. *J Am Coll Nutr* 1994; 13:73–82.

Privette TH, Wang JQ, Ingenito AJ, Terrian OM. Dentate granule cells as a central cardioregulatory site in the rat. *Brain Res* 1994; 656:295–301.

Rapoport RM, Williams SP. Role of prostaglandins in acetylcholine–induced contraction of aorta from spontaneously hypertensive and Wistar–Kyoto rats. *Hypertension* 1996; 28:64–75.

Rodrigo E, Maeso R, Munoz–Garcia R, et al. Endothelial dysfunction in spontaneously hypertensive rats: consequences of chronic treatment with losartan or captopril. *J Hypertens* 1997; 15:613–8.

Rouse D, Abramowitz J, Zhou X, et al. Plasma membrane calcium ATPase isoform expression in cultured rat mesangial cells. *Am J Physiol* 1997; 273:F76–83.

Rubattu S, et al. Influence of hypercholesterolemia on adrenal steroid metabolism and electrolyte balance in spontaneously hypertensive rats. *Endocrinology* 1993; 133:2015–21.

Rubattu S, Russo R, Gigante B, et al. Regulation of 11 beta–hydroxylase cytochrome p450 expression by cholesterol in spontaneously hypertensive rats. *J Hypertens* 1995; 13:1253–8.

Rubattu S, et al. Chromosomal mapping of quantitative trait loci contributing to stroke in a rat model of complex human disease [see comments]. *Nat Genet* 1996; 13:429–34.

Sales ME, Borda ES, Sterin–Borda L, Arregger A, Andrada EC. Role of prostaglandin E2 in alterations of the beta–adrenergic system from rat eclamptic uterus. *Biochem Pharmacol* 1995; 50:1071–7.

Schiffrin EL, Tureon A, Deng LY. Effect of chronic ETA-selective endothelin receptor antagonsim on blood pressure in experimental and genetic hypertension in rats. *Br J Pharmacol* 1997; 1 21:935–40.

Schirner M, Taube C. Different effects of aspirin on blood pressure of spontaneously hypertensive rats (SHR) with high and spontaneously low levels of blood pressure. *Br J Pharmacol* 1993; 109:900–1.

Seto S, et al. Centrally administered calcium increases the maximum vagal activation of baroreceptor reflex control of heart rate in spontaneously hypertensive rats. *J Carciovasc Pharma* 1997; 29:639–46.

Sirokman G, Humphries DE, Bing OH. Endogenous retroviral transcripts in myocytes from spontaneously hypertensive rats. *Hypertension* 1997; 30:88–93.

Skrede KK, Roshol H, Aero CE, Wiik P. Peritoneal leucocytes from spontaneously hypertensive rats have reduced chemiluminescence response and lowered sensitivity to dexamethasone in vivo. *Acta Physiol Scand* 1996; 158:169–79.

Susic O, et al. Antihypertensive action of heparin: role of the renin–angiotensin aldosterone system and prostaglandins. *J Clin Pharmacol* 1993; 33:342–7.

Takeda Y, et al. 11 beta–Hydroxysteroid dehydrogenase activity in mesenteric arteries of spontaneously hypertensive rats. *Clin Exp Pharmacol Physiol* 1993; 20:627–31.

Tang Z, et al. Effect of antihypertensive drugs of glycemic control on antioxidant enzyme activities in spontaneously hypertensive rats with diabetes. *Nephron* 1997; 73:323–30.

Tsushima H, Fujimoto S. alpha–adrenoceptor subtype in the hypothalamic paraventricular nucleus involved in the regulation of urine production: comparison between Wistar Kyoto and spontaneously hypertensive rats. *Jpn J Pharmacol* 1997; 74:95–8.

Uchida A, Nakata T, Hatta T, et al. Reduction of insulin resistance attenuates the development of hypertension in sucrose–fed SHR. *Life Sci* 1997; 61:455–64.

Valentin JP, Mazbar SA, Humphreys MH. Long–term captopril treatment restores natriuresis after carotid baroreceptor activation in the SHR. *Am J Physiol* 1997; 273:R70–9.

Wagner J, Klotz S, Haufe CC, et al. Progression of renal failure after subtotal nephrectomy in transgenic rats carrying an additional renin gene [TGR(mREN2)27]. *J Hypertens* 1997; 15:441–9.

Wang X, Aukland K, Bostad L, Iversen BM. Autoregulation of total and zonal glomerular filtration rate in spontaneously hypertensive rats with mesangiolysis. *Kidney Blood Press Res* 1997; 20:11–7.

Wiesenfeld P, Michaelis OEt. Gender Differences in adrenal cortex steroid production in SHR/N–corpulent rats. *Proc Soc Exp Biol Med* 1994; 207:254–9.

Yokoshiki H, Kohya T, Tomita F, et al. Restoration of action potential duration and transient outward current by regression of left ventricular hypertrophy. *J Mol Cell Cardiol* 1997; 29:1331–9.

Yoshida M, Kikukawa M, Hisa H, Satoh S. Modulation by nitric oxide and prostaglandin of the renal vascular response to angiotensin 11(3–8). *Br J Pharmacol* 1996; 117:885–90.

Zhu YC, et al. Effects of angiotensin–converting enzyme inhibition and angiotensin II ATi receptor antagonism on cardiac parameters in left ventricular hypertrophy. *Am J. Cardiol.* 1997; 80:110A–117A.

Zimlichman R, Zaidel L, Nofech–Mozes S, et al. Hyperinsulinemia induces myocardial infarctions and arteriolar medial hypertrophy in spontaneously hypertensive rats. *Am J Hypertens* 1997; 10:646–53.

Jacob HJ, Lindpaintner K, Lincoln SE, et al. Genetic mapping of a gene causing hypertension in the stroke–prone spontaneously hypertensive rat. *Cell* 1999; 67:213–24.

Jacob HJ, Brown DM, Bunker RK, et al. A genetic linkage map of the laboratory rat, *Rattus norvegicus. Nat Genet* 1995; 9:63–9.

Vesely, et al., 1996. "Atrial natriuretic peptides negatively and positively modulate circulating endothelin in humans." Metabolism: Clin & Exp. 45: 315–319.

Vesely, et al., 1996. "Atrial natriuretic peptide increases adrenomedullin in the circulation of healthy humans." Life Sciences. 59: 243–254.

Vesely, et al., 1995. "Atrial natriuretic peptides and cyclic guanosine monophosphate metabolism." Am J Med Sci. 310: 143–149.

* cited by examiner

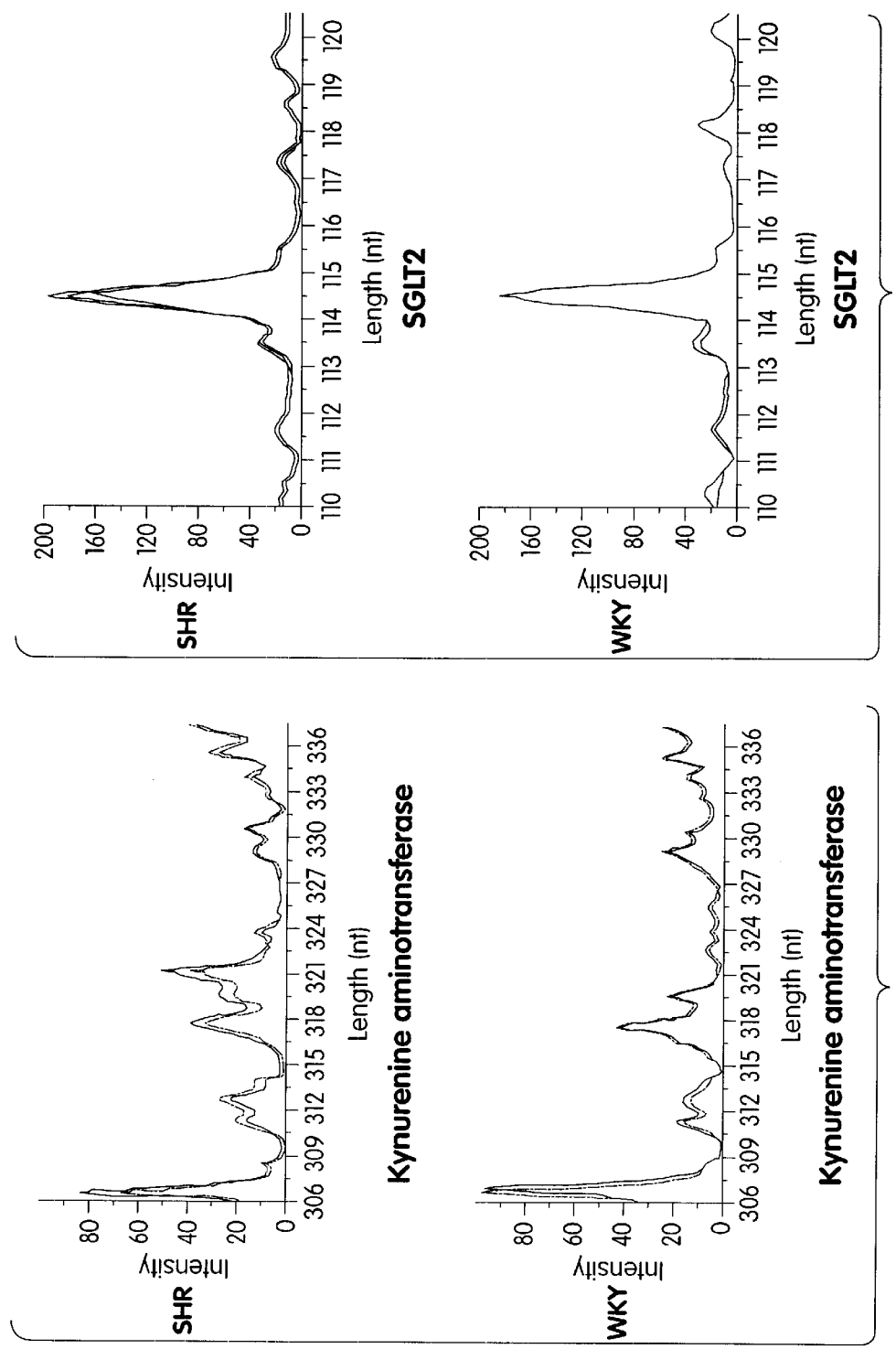

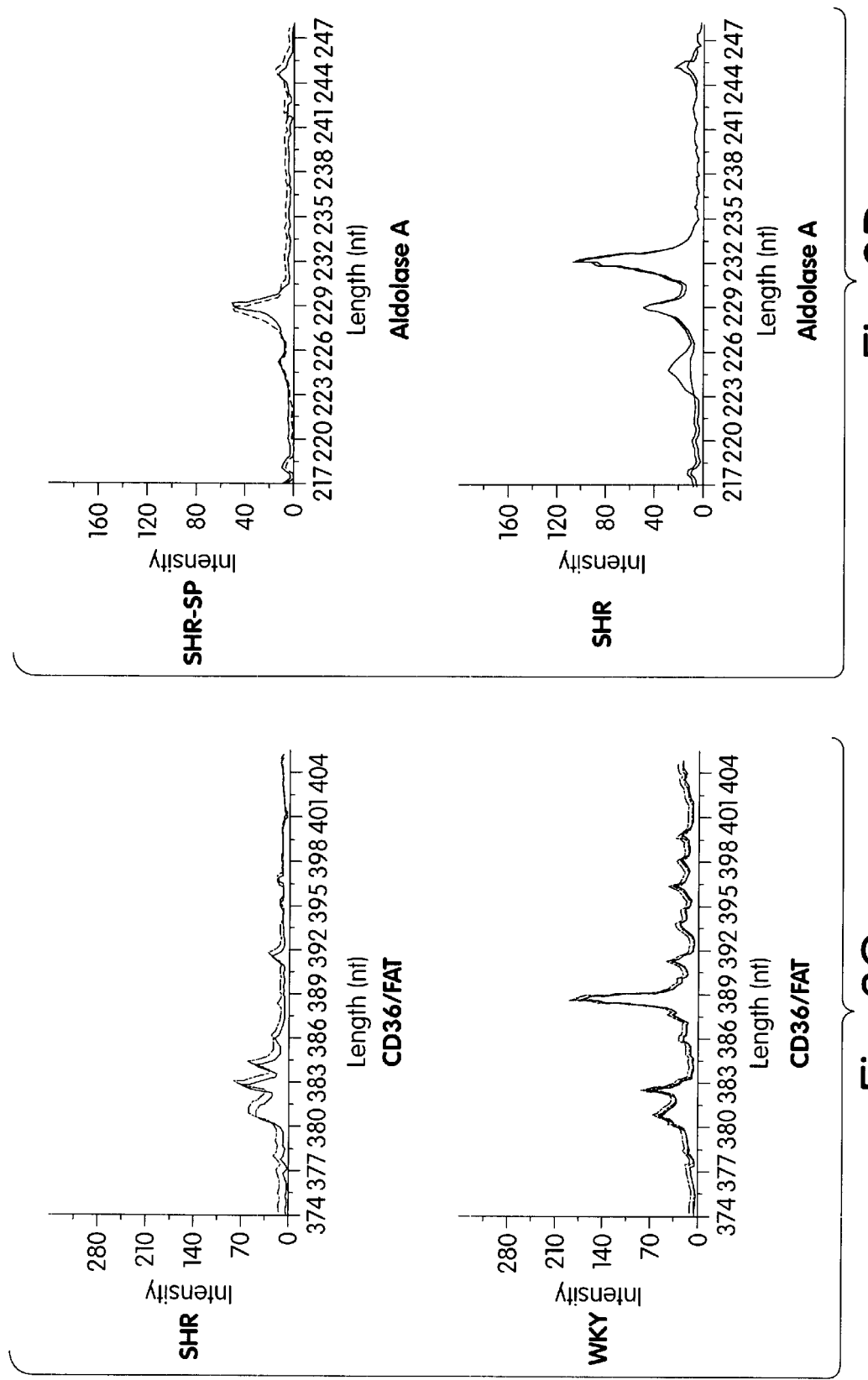

SGLT2 Variant
```
            629                  648
SHR     EEVAATTRRQEDISEDPSWA    (SEQ ID NO:1)
WKY     EEVAATTRRLEDISEDPSWA    (SEQ ID NO:9)
Human   EEAAAAARRLEDISEDPSWA    (SEQ ID NO:10)
Rabbit  EEEAAAARRLEDINEDPRWS    (SEQ ID NO:11)
Pig     EEEEAQKRKLTDTSEKPLWK    (SEQ ID NO:12)
```

Fig. 4A

Kynurenine Aminotransferase Variant
```
            16                 34
SHR       NLWVEFGKLTKGYDVVNLG   (SEQ ID NO:2)
WKY       NLWVEFGKLTKEYDVVNLG   (SEQ ID NO:13)
Human     NPWVEFVKLASEHDVVNLG   (SEQ ID NO:14)
Nematode  SIWVEFTTLAAETKAVNLG   (SEQ ID NO:15)
```

Fig. 4B

CD36/FAT Variants
```
            148                                          191
SHR-SP  YTNSFVQGVLNSLIKKSKSSMFQTRSLKELLWGYKDPFLSLVPY  (SEQ ID NO:3)
SHR     YQNSFFQGVLNIFIKKSKSSMFQTRSLKELLWGYEDPFLSLIPY  (SEQ ID NO:16)
WKY     YTNSFVQGVLNSLIKKSKSSMFQTRSLKELLWGYKDPFLSLVPY  (SEQ ID NO:17)
Mouse   YQNSFVQVVLNSLIKKSKSSMFQTRSLKELLWGYKDPFLSLVPY  (SEQ ID NO:18)

213                                              257
SHR-SP  VFNGKDNISKVAIIDTYKGKRNLSYWKSYCDMINGTDAASFPPFG  (SEQ ID NO:4)
SHR     VFNGKDNISKVAIIDTYKGKRNLSYWESYCDMINGTDAASFPPLG  (SEQ ID NO:19)
WKY     VSNGKDNISKVAIIDTYKGKRNLSYWKSYCDMINGTDAASFPPLG  (SEQ ID NO:20)
Mouse   VFNGKDNISKVAIIESYKGKRNLSYWPSYCDMINGTDAASFPPFV  (SEQ ID NO:21)
```

Fig. 4C

Aldolase A Variant
```
            12                31
SHR-SP  GEHTPSSLAIVENANVLARY   (SEQ ID NO:5)
SHR     GEHTPSSLAIMENANVLARY   (SEQ ID NO:22)
WKY     GEHTPSSLAIMENANVLARY   (SEQ ID NO:23)
Mouse   GEHTPSALAIMENANVLARY   (SEQ ID NO:24)
Human   GEHTPSALAIMENANVLARY   (SEQ ID NO:25)
Seal    GEHTPSALAIMENANVLARY   (SEQ ID NO:26)
Dog     GEHTPSALAIMENANVLARY   (SEQ ID NO:27)
Rabbit  GEHTPSALAIMENANVLARY   (SEQ ID NO:28)
```

Fig. 4D

Pepronatriodilatin Variant
```
              89                        111
SHR-SP  SQRDGGALGRSPWDPSDRSALLK    (SEQ ID NO:6)
SHR     SQRDGGALGRGPWDPSDRSALLK    (SEQ ID NO:29)
WKY     SQRDGGALGRSPWDPSDRSALLK    (SEQ ID NO:30)
Human   AQRDGGALGRGPWDSSDRSALLK    (SEQ ID NO:31)
Pig     AQRDGGALGRGPWDASDRSALLK    (SEQ ID NO:32)
Horse   AQRDGGALGRGSWDSSDRSALLK    (SEQ ID NO:33)
```

Fig. 4E

Alpha-Cardiac Myosin Variant
```
             999                                      1035
SHR-SP  ALQEAHQQALDDLQAEEDKVNTLIKSKVKLEQQVDDL   (SEQ ID NO:7)
SHR     ALQEAHQQALDDLQAEEDKVNTLTKSKVKLEQQVDDL   (SEQ ID NO:34)
WKY     ALQEAHQQALDDLQAEEDKVNTLTKSKVKLEQQVDDL   (SEQ ID NO:35)
Mouse   ALQEAHQQALDDLQAEEDKVNTLTKSKVKLEQQVDDL   (SEQ ID NO:36)
Human   ALQEAHQQALDDLQAEEDKVNTLTKAKVKLEQQVDDL   (SEQ ID NO:37)
```

Fig. 4F

Alpha-Tubulin Variant
```
              314                                              363
SHR      ACCLLYRGDVVPKDVNAAIATIKTKRSIQFVDWCPTGFKVGINYQPPTVV   (SEQ ID NO:8)
WKY      ACCLLYRGDVVPKDVNAAIATIKTKRTIQFVDWCPTGFKVGINYQPPTVV   (SEQ ID NO:38)
Mouse    ACCLLYRGDVVPKDVNAAIATIKTKRTIQFVDWCPTGFKVGINYQPPTVV   (SEQ ID NO:39)
Chicken  ACCLLYRGDVVPKDVNAAIATIKTKRTIQFVDWCPTGFKVGINYQPPTVV   (SEQ ID NO:40)
Human    ACCMLYRGDVVPKDVNAAIATIKTKRTIQFVDWCPTGFKVGINYQPPTVV   (SEQ ID NO:41)
Fluke    ACCMLYRGDVVPKDVNAAIATIKTKRTIQFVDWCPTGFKVGINYQPPTVV   (SEQ ID NO:42)
```

Fig. 4G

GENES AND PROTEINS PREDICTIVE AND THERAPEUTIC FOR STROKE, HYPERTENSION, DIABETES AND OBESITY

FIELD OF THE INVENTION

The present invention discloses a set of genes which have been demonstrated to be anomalously regulated (i.e., dysregulated) in a model of combining a pathophysiological predisposition towards stroke, hypertension, diabetes and obesity. The present invention also relates to methods of treating and/or preventing stroke, hypertension, diabetes or obesity by the administration of the nucleic acids or protein products (and derivative and analogs thereof) of the GENE SET which are defective and/or are of low abundance in humans. The present invention further relates to methodologies of diagnosis, prognosis and screening for alleles of the GENE SET which may cause or predispose to the aforementioned diseases.

BACKGROUND OF THE INVENTION

Prevalent human diseases such as hypertension, non-insulin dependent diabetes (NIDDM), stroke, and obesity (dyslipidemia) have been shown to possess a significant genetic component composed of multiple, perhaps numerous, underlying genetic defects. Human Metabolic Syndrome X, a relatively common but poorly understood disorder, has been shown to possess a significant genetic component which is comprise of an association of the pathophysiologies of hypertension, insulin resistance, dyslipidemia and abdominal obesity. See e.g., Ferrannini, et al., 1987. *New Engl. J. Med.* 317:350–357; Kaplan, 1989. *Arteriosclerosis* 9:335–344. Given the prevalence of this combination of diseases, many research groups have focussed their efforts upon determining the etiology (i.e., the primary causative genetic defects) of Metabolic Syndrome X in humans and closely-associated animal models.

The most successfully studied of these aforementioned diseases to date is hypertension, with strong evidence nucleotide sequence variants, with their associated amino acid residue substitutions, within a total of 11 human genes affect blood pressure. See e.g., Shimkets, et al., 1994. *Cell* 79(3):407–414; Simon, et al., 1997. *Nat. Genet.* 17(2):171–178; Geller, et al., 1998. *Nat. Genet.* 19(3):279–281. While in all probability these variants, in toto, account for only a fraction of the variation in blood pressure within the general population, they, nonetheless, serve to illustrate the potential that the etiology of many such diseases may involve the interaction of a large number of genetic components. As the majority of the genetic components of complex diseases such as human Metabolic Syndrome X have yet to be elucidated, a comprehensive analysis for the genetic defects responsible for the phenotype was undertaken in the present invention within a closely-associated animal model of this syndrome.

The most widely-utilized and generally-accepted model of human Metabolic Syndrome X is the spontaneously hypertensive rat (SHR), which is characterized by the pathophysiologies of salt-induced hypertension, insulin resistance and increased abdominal fat. See e.g., Yamori, 1984. *Experimental and Genetic Models of Hypertension* In: Handbook of Hypertension (Elsevier Science Publishers, New York, N.Y.). While many genetic loci have been linked to various aspects of the SHR phenotype relative to those of the Wistar Kyoto (WKY) control strain, only a single gene defect has been implicated as a causative factor in the phenotype. See e.g., Aitman, et al., 1997. *Nat. Genet.* 16(2):197–201; Clark, et al., 1996. *Hypertension* 28(5):898–906; Bottger, et al., 1996. *J. Clin. Invest.* 98(3):856–862. In addition, a spontaneous variant of the SHR was found which, in addition to the features of human Metabolic Syndrome X, undergoes severe hemmhoragic or ischemic stroke. This strain was designated SHR stroke-prone (SHR-SP). See e.g., Okamoto, et al., 1974. *Circ. Res.* 33/34:I-143–153; Rabattu, et al., 1996. *Nat. Genet.* 16(4):364–367. Prior to the present invention, the gene(s) influencing the manifestation and latency period of stroke within SHR-SP animals have also not been identified.

In order to identify the primary genetic defects leading to the phenotype of the SHR and SHR-SP, the present invention has included a comprehensive gene expression analysis utilizing the GeneCalling® technology to identity the majority of differentially-expressed genes between the strains of animals that were used for genetic linkage analysis. GeneCalling® not only identifies both known and novel differentially-expressed genes, but also identifies sequence variations in complementary DNA (cDNA) between the various strains being compared. These variations detected by GeneCalling® can include, but are not limited to, insertions, deletions and single base-pair changes.

In order to identify, in the most efficacious manner possible, which of the differentially-expressed genes may contribute directly to the phenotype, the genes were placed on the physical map of the rat using a radiation hybrid panel. Given the statistical improbability of each "event" occurring by chance, genes which were found to be both differentially-expressed within the different animal strains and tissues/organs and to map within quantitative trait loci (QTL), were deemed to have a high probability of possessing mutations which would affect the phenotype.

Presented herein is the first comprehensive organ survey of differences in gene expression in a genetic disease model coupled with a comprehensive mapping and mutation detection strategy to identify the gene(s) responsible for causing or predisposing to these aforementioned disease traits.

It should be noted that the citation or discussion of a reference herein shall not be construed as an admission that such is prior art to the present invention.

SUMMARY OF THE INVENTION

The present invention discloses the use of genes within a GENE SET, or mutations of the genes within the GENE SET, as diagnostics and therapeutics for disease.

More specifically, the present invention discloses nucleic acid sequences comprising the genes of a GENE SET, the proteins encoded therefrom and derivatives, analogs and mutations thereof, for use in the diagnosis, prognosis and screening, as well as the treatment, both prophylactic and therapeutic, of diseases such as hypertension, diabetes (insulin resistance), obesity/dyslipidemia and stroke (ischemic disease).

Further disclosed herein are methodologies of diagnosis, prognosis, and screening by detecting genes from the GENE SET. Diagnostic, prognostic and screening kits are also provided.

Additionally, the present invention also discloses methods of screening for modulators of GENE SET activity which affect hypertension, diabetes, obesity and both the latency period and severity of stroke.

BRIEF DESCRIPTION OF THE FIGURES

In order that the present invention disclosed herein is better understood and appreciated, the following detailed description is set forth.

FIG. 4: Illustrates the variation of amino acid residues found between WKY, SHR and SHR-SP genes. Predicted amino acid residue variation, based on nucleotide changes found in cDNAs encoding the proteins shown, are indicated by underlining. The first and last amino acid are numbered relative to the start of translation, as indicated in the corresponding GenBank entry.

Figure 1:
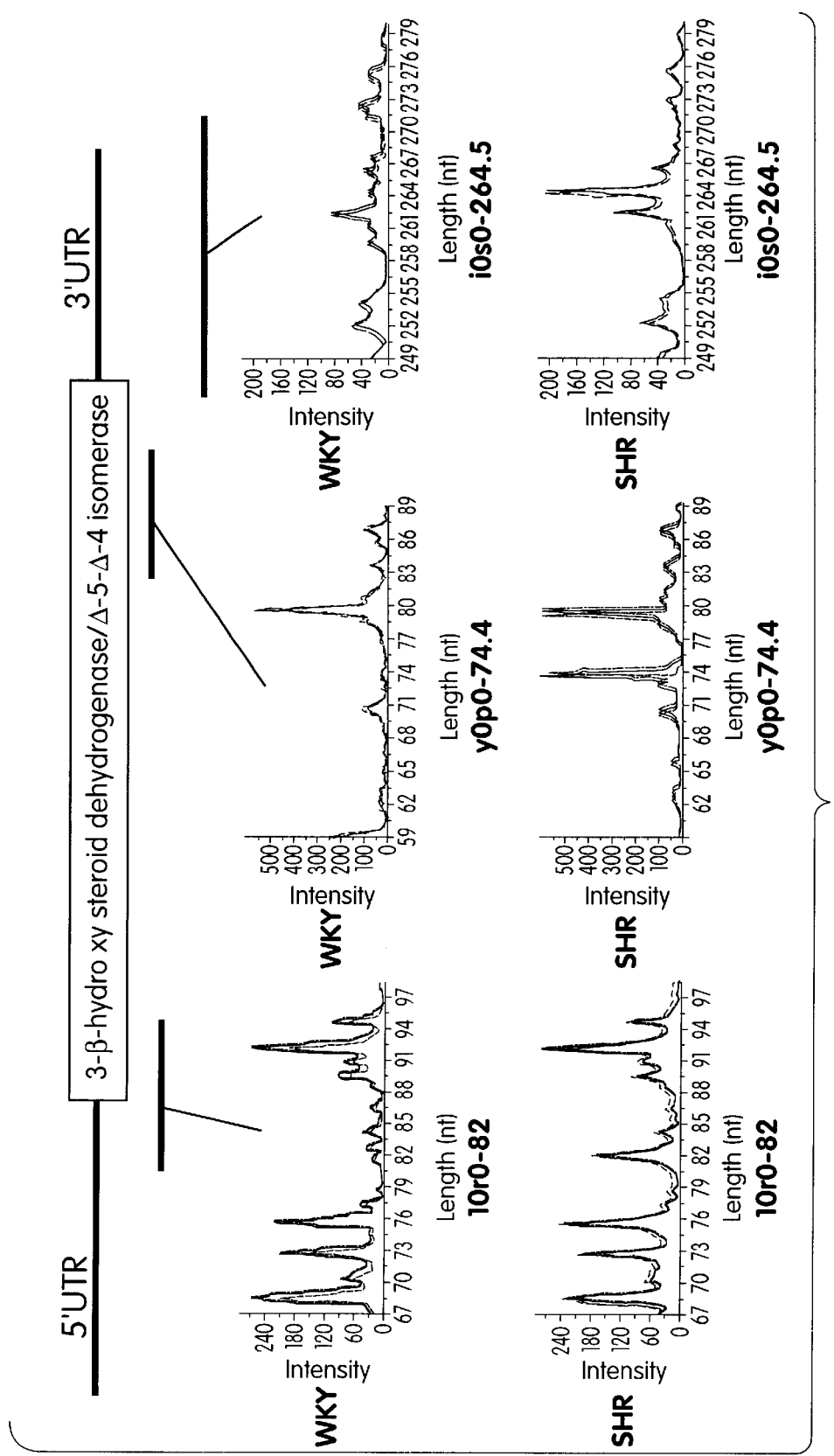
FIG. 1: Illustrates multiple GeneCalling® fragments derived from the same gene. Independent gene fragments from 3-β-hydroxysteroid dehydrogenase/Δ-5-Δ-4 isomerase were found to be differentially-expressed, and the region of the cDNA from which they were derived is indicated. The red vertical line indicates the peak of the expression difference. Fragment length in nucleotides is indicated on the x-axis, relative peak intensity is indicated on the y-axis. Each trace represents the composite of multiple reactions from a single animal.

Also shown are the amino acid sequences of the mutant rat proteins consisting of: SGLT2 (SEQ ID NO:1 and 9–12); kynurenine aminotransferase (SEQ ID NOS:2 and 13–15); FAT/CD36 (SEQ ID NOS:3, 4 and 16–21); aldolase A (SEQ ID NOS:5 and 22–28); prepronatriodilatin (SEQ ID NOS:6 and 29–33); α-cardiac myosin (SEQ ID NOS:7 and 34–37) and α-tubulin (SEQ ID NOS:8 and 38–42).

Table 1: Total gene expression differences by genotype and organ. For each set of organs from each animal genotype that was compared, the number of gene fragments analyzed, the number of differences found and the percentage differences are illustrated.

Table 2: Differential gene expression between the SHR and WKY rats. Differential gene expression across a total of five (5) tissues is illustrated, where a "+" indicates increased mRNA abundance in the SHR and a "−" indicates a decreased MRNA abundance in the SHR. The chromosome to which the gene maps is provided and a "*" denotes that the gene maps to a position within a known QTL. In addition, amino acid residue substitutions which were identified by the present invention are also provided, where applicable.

Table 3: Differential gene expression between the SHR-SP and SHR rats. Differential gene expression across a total of five (5) tissues is presented, where a "+" indicates increased MRNA abundance in the SHR-SP and a "−" indicates a decreased mRNA abundance in the SHR-SP. The chromosome to which the gene maps is provided and a "*" denotes that the gene maps to a position within a known QTL. In addition, amino acid residue substitutions which were identified by the present invention are also provided, where applicable.

DETAILED DESCRIPTION OF THE INVENTION

The present invention discloses a GENE SET comprising a total of 6 genes which were found to be both differentially-expressed and mutated (i.e., possessing amino acid residue substitutions) between disease and control states in genetic rat models of hypertension, obesity, diabetes and stroke. The GENE SET (hereinafter "GENE SET") includes: (i) CD36 (also known as fatty acid transport protein (FAT)); (ii) sodium dependent glucose co-transporter (SGLT2); (iii) aldolase A; (iv) kynurenine aminotransferase; (v) α-cardiac myosin and (vi) α-tubulin; as well as the previously-described mutation in the atrial natriuretic peptide (ANP).

Accordingly, the present invention relates to mutants of the proteins which are encoded by aforementioned GENE SET (and derivatives, fragments and homologs thereof) and the nucleic acids which encode them (and derivatives, fragments and homologs thereof), which function so as to increase predisposition to stroke, hypertension, diabetes and obesity.

The present invention relates to methods of diagnosis, prognosis and screening for stroke, hypertension, diabetes and obesity. In one embodiment, subjects are screened for a mutant allele of the GENE SET. In another embodiment, subjects are screened to differentiate the expression of mRNAs derived from the GENE SET, relative to their expression within controls.

The present invention also relates to methods of screening members of the GENE SET for the ability to affect the onset of, or predisposition to, hypertension, diabetes (insulin resistance) or obesity (dyslipidemia) or stroke, and to methodologies of screening for modulators (i.e., agonists, antagonists and inhibitors) of these genes.

(1) Mutated GENE SET

Proteins produced from the GENE SET, and mutants of derivatives, fragments, homologs and analogs of GENE SET proteins and the nucleic acids encoding the mutants, protein derivatives and protein analogs are disclosed by the present invention. The GENE SET mutants can be proteins possessing substitutions, deletions or insertions of one or more amino acid residues within the amino acid sequence wild-type GENE SET protein. Preferably, the GENE SET mutants are capable of binding to an anti-GENE SET antibody.

In another embodiment of the present invention, the GENE SET mutant increases latency to hypertension or stroke in stroke-prone rats (e.g., rats possessing the stroke-predisposing locus located on chromosome 1) which are fed a high salt diet (for example, but not limited to, a diet of 17.5% protein, 3.7 mg/g body weight $Na^+$, 6.3 mg/kg body weight $K^+$, and 0.03 mg/g body weight methionine and 1% NaCl drinking water).

Derivatives or analogs of GENE SET include, but are not limited to, those molecules comprising regions which are substantially homologous to the wild-type GENE SET or mutant GENE SET, or fragments thereof. For example, in various embodiments, at least 60–70% homology, preferably 70–80% homology, more preferably 90–95% homology and most preferably ≧95% homology over an amino acid sequence of identical size or when compared to an aligned sequence in which the alignment is performed by a computer homology program known within the art, or whose encoding nucleic acid is capable of hybridizing to a coding GENE SET sequence, under stringent, moderately stringent, or non-stringent conditions.

The GENE SET, as well as fragments, derivatives, homologs and analogs GENE SET, of the present invention can be produced by various methods known within the art. The manipulations which result in their production can occur at the gene or protein level. For example, the cloned GENE SET gene sequence can be modified by any of numerous strategies known within the art. See e.g., Sambrook, et al., 1990. *Molecular Cloning, A Laboratory Manual,* 2ed. (Cold Spring Harbor Laboratory Press, Cold Spring Harbor, N.Y.). The sequence of interest may be cleaved at appropriate sites with a restriction endonuclease (RE), followed by further enzymatic modification (if necessary), isolated, and ligated in vitro. In the production of the gene encoding a mutant, derivative or analog of the GENE SET, care should be taken to ensure that the modified gene remains within the same translational reading frame as the GENE SET and is uninterrupted by translational stop signals within the exonic region where the desired GENE SET activity is encoded.

The GENE SET-encoding nucleic acid sequence may be mutated in vitro or in vivo, to make changes within the coding regions (e.g., amino acid substitutions, additions or deletions) as well as to create and/or destroy translation, initiation, and/or termination sequences, or to form new restriction endonuclease sites or destroy pre-existing ones, to facilitate further in vitro modification. Any technique for mutagenesis known within the art may be utilized including, but not limited to, chemical mutagenesis; in vitro site-directed mutagenesis (see e.g., Hutchinson, et al., 1978. *J. Biol. Chem.* 253:6551); use of TAB7® linkers (Pharmacia), and the like.

Manipulations of the GENE SET sequence may also be made at the protein level.

Included within the scope of the invention are GENE SET protein fragments or other derivatives or analogs which are differentially-modified during or after translation (e.g., by glycosylation, acetylation, phosphorylation, arnidation, derivatization by known protecting/blocking groups, proteolytic cleavage, linkage to an antibody molecule or other cellular ligand, etc). Any of numerous chemical modifications may be performed by known techniques, including but not limited to specific chemical cleavage by cyanogen bromide, trypsin, chymotrypsin, papain, V8 protease, NaBH$_4$; acetylation, formylation, oxidation, reduction; metabolic synthesis in the presence of tunicamycin; etc. Particularly included within the scope of the present invention are those modifications which reduce the level or activity of the GENE SET.

In addition, mutant GENE SET proteins (or analogs and derivatives thereof) which mediate the desired activity in vivo or in vitro, may be synthesized by use of a peptide synthesizer. Furthermore, if desired, non-classical amino acids or chemical amino acid analogs may be introduced as a substitution or addition into the GENE SET sequence. Non-classical amino acids include, but are not limited to: the D-isomers of the common amino acids, α-amino isobutyric acid, 4-aminobutyric acid, Abu, 2-amino butyric acid, γ-Abu, ϵ-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acid may either be D (dextrorotary) or L (levorotary) isomers.

In another embodiment of the present invention, the GENE SET derivative is a chimeric, or fusion, protein comprising an GENE SET protein or fragment thereof (preferably consisting of at least 10 amino acids of the GENE SET protein or a mutant GENE SET protein) joined at its amino- or carboxyl-terminus via a peptide bond to an amino acid sequence of a different protein. In one embodiment, such a chimeric protein is produced by recombinant expression of a nucleic acid encoding the protein (i.e., comprising a GENE SET-coding sequence joined in-frame to a coding sequence for a different protein). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques (e.g., by use of a peptide synthesizer). Chimeric genes comprising portions of the wild-type GENE SET or the mutant GENE SET fused to any heterologous protein-encoding sequences may be constructed. A specific embodiment of the present invention discloses a chimeric protein comprising a fragment of GENE SET or mutant GENE SET of at least six amino acids.

Additionally, due to the degeneracy of nucleotide-coding sequences, other DNA sequences which encode substantially the same amino acid sequence as the mutant GENE SET of the present invention may be utilized in the practice of the present invention. The genes indigenous to the mutant GENE SET may be obtained by alteration of nucleotide sequences comprising all or portions of GENE SET gene by the substitution of different codons which encode the desired amino acid. For example, one or more amino acid residues within the sequence may be substituted by another amino acid of a similar polarity which acts as a functional equivalent, resulting in a "silent alteration." Substitutes for an amino acid within the sequence may be selected from other members of the class to which the amino acid belongs. For example, the nonpolar (hydrophobic) amino acids include, but are not limited to, alanine, leucine, isoleucine, valine, proline, phenylalanine, tryptophan and methionine. The polar neutral amino acids include, but are not limited to, glycine, serine, threonine, cysteine, tyrosine, asparagine, and glutamine. The positively charged (basic) amino acids include, but are not limited to, arginine, lysine and histidine. The negatively charged (acidic) amino acids include, but are not limited to, aspartic acid and glutamic acid.

In addition, the present invention discloses mutant GENE SET molecules, containing the aforementioned mutations for mutant GENE SET molecules.

(2) Nucleic Acid Sequences and Proteins of the GENE SET

GENE SET proteins and nucleic acids can be obtained by any methodology known within the art. The GENE SET amino acid and nucleotide sequences for, inter alia, human, rat, hamster, dog, mouse, bovine, porcine, equine, dogfish, *Drosophila melanogaster* and Xenopus are available in the public databases (e.g., GenBank).

The amino acid sequence of a rat FAT/CD36 amino acid sequence (Acc. No. L19658) is set forth below:

MGCDRNCGLITGAVIGAVLAVFGGILMPVGDLLIEKTIKREVVLEE
GTIAFKNWVKTGTTVYRQFWVFDVQNPEEVAKNSSKIK
VIQRGPYTYRVRYLAKENITQDPKDSTVSFVQPNGAIFEP
SLSVGTENDNFTVLNLAVAAAPHIYTNSFVQGVLN
SLIKKSKSSMFQTRSLKELLWGYKDPFLSLVPYPISTTVGV
FYPYNNTVDGVYKVSNGKDNISKVAIIDTYKGKRNLSY
WESYCDMINGTDAASFPPLGEKSRTLRFFSSDICRSI
YAVFESEVNLKGIPVYRFVLPANAFASPLQNPDNHCFCTE
KVISNNCTSYGVLDIGKCKEGKPVYNSLPHFLHASPDVS
EPIEGLNPTEDEHRTYLDVEPITGFTLQFSKRLQVNI
LVKPARKIEALKNLKRPYIVPILWLNETGTIGDEKAEMFRNQVT
GKIKLLGLVEMVLLGVGVVMFVAFMISYCACRSKNGK(SEQ ID NO:44)

Any eukaryotic cell potentially can serve as the nucleic acid source for the isolation of GENE SET nucleic acids. The nucleic acid sequences of the GENE SET may be isolated from vertebrate, mammalian, human, porcine, bovine, feline, avian, equine, canine, primate, and like sources. The DNA may be obtained by standard protocols known within the art from cloned DNA (e.g., a DNA "library"), by chemical synthesis, by cDNA cloning, or by the cloning of genomic DNA (or fragments thereof) purified from the desired cell. See e.g., Sambrook, et al., 1990. *Molecular Cloning, A Laboratory Manual,* 2d ed. (Cold Spring Harbor Laboratory Press, Cold Spring Harbor, N.Y.); Glover, 1985. *DNA Cloning: A Practical Approach* (MRL Press, Ltd., Oxford, U.K.). Clones which are derived from genomic DNA may contain regulatory and non-coding, intron DNA regions, in addition to coding, exonic regions; whereas clones which are derived from cDNA will contain only coding, exon sequences. Following isolation, the sequence of interest is then molecularly-cloned into a suitable vector for propagation.

In the molecular cloning of the gene from complementary DNA (cDNA), the EDNA is synthesized by reverse transcription from total cellular RNA or poly(A)$^+$ mRNA by methods which are well-known within the art. The gene(s) of interest may also be obtained from genomic DNA, wherein random DNA fragments are generated (e.g., by use of restriction endonucleases or by mechanical shearing), some of which will encode the desired sequence(s). The linear DNA fragments may then be separated as a function of their size by standard techniques including, but not limited to, agarose and polyacrylamide gel electrophoresis and column chromatography.

Once the DNA fragments have been generated, identification of the specific DNA fragment containing all or a portion of the GENE SET gene may be accomplished in a number of ways. In a preferred embodiment of the present invention, a GENE SET gene is isolated by use of the polymerase chain reaction (PCR), which can be utilized to amplify the desired GENE SET sequence within a genomic or cDNA library, or directly from genomic DNA or cDNA which has not been incorporated into a library. Synthetic oligonucleotides may then be utilized as primers in PCR-mediated amplification of sequences from an RNA or DNA source, preferably from a cDNA library, of potential interest. In addition, several different degenerate primers may be synthesized for use in the PCR amplification reactions. The PCR amplification reaction may be performed, for example, by use of a Perkin-Elmer Cetus® Thermal Cycler and Taq polymerase (Gene AmpJ).

It is also possible to vary the stringency of hybridization conditions utilized during the priming of the PCR amplification reactions, to allow for greater or lesser degrees of nucleotide sequence similarity between the known GENE SET nucleotide sequence and the nucleic acid of an GENE SET homolog being isolated. For cross-species hybridization, low stringency conditions are preferred. For same-species hybridization, moderately stringent conditions are preferred. Following successful amplification of a fragment or segment of a GENE SET homolog, that segment may be molecularly-cloned, sequenced and utilized as a probe to isolate a complete cDNA or genomic clone. This, in turn, will permit the subsequent determination and isolation of the gene's complete nucleotide sequence. Alternately, PCR amplification may also be used to detect and quantitate GENE SET mRNA levels.

Additionally, a portion of a GENE SET gene or its associated mRNA (or a fragment thereof) may be purified, or an oligonucleotide synthesized, and the generated DNA fragments may be analyzed by nucleic acid hybridization to the labeled probe. See e.g., Benton & Davis, 1977. *Science* 196:180; Grunstein & Hogness, 1975. *Proc. Natl. Acad. Sci. U.S.A.* 72:3961. Those DNA fragments which possess substantial homology to the labeled oligonucleotide probe will hybridize. GENE SET nucleic acids may be also identified and isolated by expression cloning using, for example, anti-GENE SET antibodies for selection. Alternatives to obtaining the GENE SET DNA by cloning or amplification include, but are not limited to, chemically-synthesizing the gene sequence itself from the known GENE SET sequence or synthesizing a cDNA from the mRNA encoding the GENE SET protein of interest. It should be noted that the use of other methodologies is possible and within the scope of the present invention.

Once a clone has been obtained, its identity may be ascertained by nucleic acid sequencing and computer database-mediated comparison to known GENE SET sequences. DNA sequence analysis may be performed by any techniques known within the art including, but not limited to: chemical-based sequencing (see Maxam & Gilbert, 1980. *Meth. Enzymol.* 65:499–560); enzymatic dideoxynucleotide chain termination sequencing (see Sanger, et al., 1977. *Proc. Natl. Acad. Sci. U.S.A.* 74:5463); T7 DNA polymerase sequencing (see Tabor & Richardson, U.S. Pat. No. 4,795,699); automated DNA sequenator (e.g., Applied Biosystems, Foster City, Calif.) or the sequencing methodology described in PCT Publication WO 97/15690.

Nucleic acids which are hybridizable to a GENE SET nucleic acid (e.g., possessing a nucleotide sequence homologous or complementary to SEQ. ID NO:3 or NO:6), or a derivative or analog thereof, may be isolated by nucleic acid hybridization under conditions of low, moderate or high stringency. By way of example and not limitation, procedures using such conditions of low stringency are as follows (see also e.g., Shilo & Weinberg, 1981. *Proc. Natl. Acad. Sci. USA* 78:6789–6792): filters containing immobilized DNA were pre-hybridized for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 $\mu$/ml denatured salnon sperm DNA. Hybridizations were performed in the same solution with the following modifications: 0.02% PVP, 0.02% Ficoll, 0.2% BSA, 100 $\mu$g/ml salmon sperm DNA, 10% (wt/vol) dextran sulfate and 5–20×10$^6$ cpm $^{32}$P-labeled probe was utilized. The filters were incubated in hybridization mixture for 18–20 hours at 40° C., and then washed for 1.5 hour at 55° C. in a solution containing 2×SSC, 25 mM Tris-HCl (pH 7.4), 5 mM EDTA and 0.1% SDS. The wash solution was then replaced with fresh solution and the filters were re-incubated for an additional 1.5 hour at 60° C. The filters were blotted dry and autoradiographed. If necessary, filters were washed for a third time at 65–68° C. and re-exposed to X-ray film. Various other conditions of low stringency hybridization which are well-known within the art may be utilized for low stringency hybridization protocols (e.g., as employed for cross-species hybridizations).

By way of example, but not of limitation, procedures utilizing conditions of moderate stringency hybridization are as follows: filters containing immobilized DNA were pre-hybridized for 6 hours at 55° C. in a solution containing 6×SSC, 5×Denhardt's solution, 0.5% SDS and 100 $\mu$g/ml denatured salmon sperm DNA. Hybridizations were performed in the same solution and 5–20×10$^6$ cpm $^{32}$P-labeled probe was utilized. The filters were incubated in hybridization mixture for 18–20 hours at 55° C. and then washed twice for 30 minutes at 60° C. in a solution containing 1×SSC and 0.1% SDS. Filters were then blotted dry and autoradiographed. Other conditions of moderate stringency hybridizations which may be utilized are well-known within the art.

Again, by way of example and not of limitation, procedures utilizing conditions of high stringency hybridization were as follows: pre-hybridization of filters containing immobilized DNA was carried out for 8 hours to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters were hybridized for 48 hours at 65° C. in pre-hybridization mixture containing 100 µg/ml denatured salmon sperm DNA and 5–20×10$^6$ cpm of $^{32}$P-labeled probe. Washing of filters was done at 37° C. for 1 hour in a solution containing 2×SSC, 0.01% PVP, 0.01% Ficoll and 0.01% BSA. This was followed by a wash in 0.1×SSC at 50° C. for 45 minuets prior to autoradiography. Other conditions of high stringency hybridization which may be used are well-known within the art.

Nucleic acids encoding derivatives and analogs of GENE SET proteins, GENE SET anti-sense nucleic acids and primers which can be utilized to detect mutant GENE SET alleles and GENE SET gene expression are disclosed by the present invention. As used herein, a "nucleic acid encoding a fragment or portion of an GENE SET protein" refers to a nucleic acid encoding only the recited fragment or portion of the GENE SET protein, and not the other contiguous portions of the GENE SET protein as a continuous sequence.

GENE SET proteins (and derivatives, analogs and fragments thereof) of GENE SET proteins may be obtained by any method known within the art including, but not limited to, recombinant expression methods, purification from natural sources, chemical synthesis and the like. For example, GENE SET proteins may be obtained by recombinant protein expression techniques, wherein the GENE SET gene or portion thereof is inserted into an appropriate cloning vector for expression within a particular host cell. A large number of vector-host systems known within the art may be used. Possible vectors include, but are not limited to, bacteriophage (e.g., lambda derivatives); plasmids (e.g., pBR322, pUC plasmid derivatives or the Bluescript vector (Stratagene)) or other vector which are well-known within the art. The insertion of the DNA fragment of interest into a cloning vector may, for example, be accomplished by ligating the fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (e.g., linkers) onto the DNA termini; these ligated linkers may comprise specific chemically synthesized oligonucleotides encoding restriction endonuclease recognition sequences. In an alternative methodology, the digested vector and GENE SET gene may be modified by homopolymeric tailing. The recombinant molecule may subsequently introduced into the host cell via transformation, transfection, infection, electroporation, and the like, to facilitate the generation of a plurality of copies of the GENE SET gene sequence of interest.

In an alternative methodology, the desired gene may be identified and isolated after insertion into a suitable cloning vector in a "shot-gun" approach. Enrichment for the desired gene by, for example, size fractionation, may be performed prior to its insertion into the cloning vector.

In specific embodiments of the present invention, transformation of host cells with recombinant DNA molecules which incorporate the isolated GENE SET gene, cDNA or synthesized DNA sequence, facilitates the generation of multiple copies of the gene. Thus, the gene may be obtained in large quantities by growing transformants, isolating the recombinant DNA molecules from the transformants and, when necessary, retrieving the inserted gene from the isolated recombinant DNA.

The nucleotide sequence encoding a GENE SET protein (or a functionally-active analog, fragment or other derivative thereof), may be inserted into an appropriate expression vector (i.e., a vector which contains the necessary elements for the transcription and translation of the inserted protein-coding sequence). Alternately, the necessary transcriptional and translational signals may also be supplied by the native GENE SET gene and/or its flanking regions. A variety of host-vector systems may be utilized to express the protein-coding sequence including, but are not limited to, mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be employed in the practice of the present invention.

Any of the methodologies previously-described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinants (i.e., genetic recombination). Expression of nucleic acid sequence encoding a GENE SET protein or peptide fragment, may be regulated by a second nucleic acid sequence so that the GENE SET protein or peptide is expressed within a host cell which has been transformed with the recombinant DNA molecule. For example, expression of a GENE SET protein may be controlled by any promoter/enhancer element known within the art including, but not limited to: (i) the SV40 early promoter region (see e.g., Bemoist & Chambon, 1981. *Nature* 290:304–310); (ii) the promoter contained in the 3'-terminus long terminal repeat (LTR) of Rous sarcoma virus (see e.g., Yamamoto, et al., 1980. *Cell* 22:787–797); (iii) the Herpesvirus thymidine kinase promoter (see e.g., Wagner, et al., 1981. *Proc. Natl. Acad. Sci. U.S.A.* 78:1441–1445); (iv) the regulatory sequences of the metallothionein gene (see e.g., Brinster, et al., 1982. *Nature* 296:39–42); (v) prokaryotic expression vectors such as the β-lactamase promoter (see e.g., Villa-Kamaroff, et al., 1978. *Proc. Natl. Acad. Sci. U.S.A.* 75:3727–3731) or the tac promoter (see e.g., DeBoer, et al., 1983. *Proc. Natl. Acad. Sci. U.S.A.* 80:21–25). Additionally, the following animal transcriptional control regions, exhibiting tissue specificity, have been utilized in transgenic animals including: (i) the elastase I gene control region which is active in pancreatic acinar cells (see e.g., Swift, et al., 1984. *Cell* 38:639–646); (ii) the insulin gene-control region which is active in pancreatic β-cells (see e.g., Hanahan, 1985. *Nature* 315:115–122); (iii) the immunoglobulin gene control region which is active in lymphoid cells (see e.g., Grosschedl, et al., 1984. *Cell* 38:647–658; (iv) the α-1-antitrypsin gene control region which is active in the liver (see e.g., Kelsey, et al., 1987. *Genes and Devel.* 1:161–171) and the β-globin gene control region which is active in myeloid cells (see e.g., Mogram, et al., 1985. *Nature* 315:338–340.

In a specific embodiment of the present invention, a vector may be used which comprises a promoter operably-linked to a GENE SET-encoding nucleic acid, one or more origins of replication and, optionally, one or more selectable markers (e.g., an antibiotic resistance gene). In another specific embodiment, an expression construct is produced by sub-cloning a GENE SET coding sequence into the EcoRI restriction site of each of the three pGEX vectors (i.e., Glutathione S-Transferase expression vectors; Smith & Johnson, 1988. *Gene* 7:31–40), thus allowing the expression of the GENE SET protein-product in the correct reading frame.

Expression vectors containing GENE SET gene inserts may be identified by the use of three general approaches: (i) nucleic acid hybridization; (ii) presence or absence of "marker" gene functions and (iii) expression of inserted nucleotide sequences. In the first approach, the presence of a GENE SET gene which has been inserted into an expression vector is detected by nucleic acid hybridization using oligonucleotide probes comprising sequences which are complementary to the aforementioned inserted GENE SET gene. In the second approach, the recombinant vector/host system is identified and selected based upon the presence or absence of certain "marker" gene functions (e.g., thymidine kinase activity, resistance to antibiotics, transformation phenotype, occlusion body formation in baculovirus, and the like) which is caused by the insertion of the GENE SET gene of interest into the vector. Specifically, if the GENE SET gene is inserted into the marker gene sequence of the vector, the recombinant species possessing the GENE SET insert may be identified by the absence of the marker gene function. In the third approach, recombinant expression vectors are identified by assaying the GENE SET protein product expressed by the recombinant. Such assays may be based, for example, upon the physical or functional properties of the GENE SET protein in various in vitro assay systems (e.g., binding of an anti-GENE SET protein antibody).

Following the isolation and identification of the recombinant DNA molecule of interest, several methodologies well-known within the art may be employed for its propagation. Once a suitable host system and growth conditions have been established, the recombinant expression vectors may be propagated and prepared in quantity. As previously disclosed, expression vectors which may be utilized include, but are not limited to the following vectors or their derivatives: human or animal viruses (e.g., vaccinia virus or adenovirus); insect viruses (e.g., baculovirus); yeast vectors; bacteriophage vectors (e.g., lambda), and plasmid and cosmid DNA vectors; and the like.

Similarly, a host cell strain may be chosen which modulates the expression of the inserted sequences or, alternately, modifies and processes the gene product in the specific fashion desired. Expression from certain promoters may be elevated by the presence of inducers; hence expression of the recombinant GENE SET protein may be controlled. Moreover, different host cells possess characteristic and/or specific mechanisms for the translational and post-translational processing and modification (e.g., glycosylation, phosphorylation of proteins), thus appropriate cell lines or host systems may be chosen to ensure the desired modification and processing of the recombinant protein is accomplished. For example, expression of the recombinant protein in a bacterial system can be used to produce an non-glycosylated core protein product; whereas expression in yeast will produce a glycosylated protein product. Similarly, expression in mammalian cells may be utilized to ensure "wild-type" glycosylation of a heterologous protein.

In other specific embodiments of the present invention, the GENE SET protein (or fragment, analog, or derivative) may be expressed as a fusion, or chimeric protein product (comprising the protein, fragment, analog, or derivative joined via a peptide bond to a heterologous protein sequence of a different protein). These chimeric products may be produced by the ligation of the appropriate nucleic acid sequences encoding the desired amino acid sequences to one another, in the proper reading frame, by methods known within the art, in the proper coding frame, and expressing the chimeric product by methods commonly known in the art. Alternatively, such a chimeric product may be made by protein synthetic techniques (e.g., by use of a peptide synthesizer). It should be noted that the cloning and subsequent expression of both cDNA and genomic DNA sequences are within the scope of the present invention.

The recombinant GENE SET proteins of the present invention may also be isolated and purified by standard methods including chromatography (e.g., ion exchange, affinity, and partition column chromatography); centrifugation; differential solubility or by any other standard technique for the purification of proteins. In an alternate embodiment, native GENE SET proteins may be purified from natural sources utilizing standard methods such as those described above (e.g., immunoaffinity purification). In another embodiment, the GENE SET proteins may be synthesized by standard chemical methods known within the art (see e.g., Hunkapiller, et al., 1984. *Nature* 310:105–111). The functional properties of the GENE SET proteins may be evaluated using any suitable assay.

(3) Methods of Treatment

The present invention discloses methodologies of treating and preventing ischemic and metabolic diseases and disorders by administration of a therapeutic compound (hereinafter designated "Therapeutics"). In one embodiment, such "Therapeutics" include GENE SET mutant proteins (and derivatives, fragments and analogs thereof), as well as nucleic acids which encode the mutant GENE SET proteins (and derivatives, fragments or analogs thereof).

In another embodiment, the protein product, which are not produced as a direct result of the diminution of the activity of an enzyme indigenous to the GENE SET, may also be utilized as a Therapeutic of the present invention. As an example, but not a limitation, the mutation (i.e., amino acid substitution) in the kynurenine aminotransferase enzyme putatively blocks the enzyme's ability to produce kynurenic acid, a small, aqueous-soluble molecule which may function as an anti-hypertensive.

In another embodiment, the Therapeutic is a mutant GENE SET protein possessing one or more substitutions of amino acid residues relative to the "wild-type" GENE SET protein The subject to which the Therapeutic is administered is preferably an animal including, but not limited to, animals such as cows, pigs, horses, chickens, cats, dogs, etc., and is preferably a mammal. In a preferred embodiment, the subject is a human.

Generally, the administration of products of a species origin or species reactivity (in the case of antibodies) which is the same species as that of the subject is preferred. Thus, in a preferred embodiment, a human mutant GENE SET protein or nucleic acid (or derivative, fragment or analog thereof) is therapeutically or prophylactically administered to a human patient.

Accordingly, in a specific embodiment of the invention, GENE SET antagonists and inhibitors including, but not limited to, anti-GENE SET antibodies and GENE SET anti-sense nucleic acids and GENE SET derivatives (e.g., which function as competitive inhibitors of GENE SET) are administered to treat or prevent stroke or ischemic disease, hypertension, diabetes or obesity.

(a) Gene Therapy

In a specific embodiment of the present invention, nucleic acids comprising a sequence encoding a GENE SET mutant protein (or derivative thereof) or a GENE SET anti-sense nucleic acid, are administered by way of gene therapy. Gene therapy refers to therapy performed by the administration of a nucleic acid to a subject. In this embodiment of the invention, the nucleic acid produces its encoded protein or is an anti-sense nucleic acid which mediates a therapeutic effect. Any of the methods for gene therapy which are well-known within the art may be utilized in the practice of the present invention. See e.g., Ausubel, et al., 1993. *Current Protocols in Molecular Biology* (John Wiley & Sons, New York, N.Y.); Kriegler, 1990. *Gene Transfer and Expression: A Laboratory Manual* (Stockton Press, New York, N.Y.).

In a preferred embodiment, the Therapeutic comprises an GENE SET nucleic acid that is part of an expression vector that expresses an GENE SET protein or fragment or chimeric protein, preferably a mutant GENE SET protein or fragment or chimeric protein, or an GENE SET anti-sense nucleic acid thereof in a suitable host. In a specific embodiment, the nucleic acid possesses a promoter which is operably-linked to the mutant GENE SET coding region or to a sequence encoding an GENE SET anti-sense nucleic acid, wherein the promoter is inducible or constitutive and, optionally, tissue-specific. In another specific embodiment, a nucleic acid is used in which the mutant GENE SET coding sequences and any other desired sequences are flanked by regions which promote homologous recombination at a desired site in the genome, thus providing for intra-chromosomal expression of the mutant GENE SET nucleic acid. See e.g., Koller & Smithies, 1989. *Proc. Natl. Acad. Sci. USA* 86:8932–8935. Delivery of the nucleic acid into a patient may be either direct, in which case the patient is directly exposed to the nucleic acid or nucleic acid-carrying vector, or indirect, in which case, cells are first transformed with the nucleic acid in vitro, then transplanted into the patient. These two approaches are known, respectively, as in vivo or ex vivo gene therapy.

In a specific embodiment, the nucleic acid is directly administered in vivo, where it is expressed to produce the encoded product. This may be accomplished by any of numerous methods known in the art including, but not limited to, constructing it as part of an appropriate nucleic acid expression vector and administering it so that it becomes intracellular by: (i) infection using a defective or attenuated retroviral or other viral vector (see e.g., U.S. Pat. No. 4,980,286); (ii) direct injection of naked DNA; (iii) use of microparticle bombardment; (iv) coating with lipids or cell-surface receptors or transfecting agents, encapsulation in liposomes, microparticles, or microcapsules; (v) by administering it in linkage to a peptide which is known to enter the nucleus; (vi) administering it in linkage to a ligand subject to receptor-mediated endocytosis which can be used to target cell types specifically-expressing the receptors and the like. In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see e.g., PCT Publications WO 92/06180 and WO 93/20221. Alternatively, the nucleic acid may be introduced intracellularly and incorporated within host cell DNA for expression, by homologous recombination. See e.g., Zijlstra, et al., 1989. *Nature* 342:435–438.

In a specific embodiment, a viral vector that contains the mutant GENE SET nucleic acid or codes for GENE SET anti-sense nucleic acid is used. For example, a retroviral vector can be used. See e.g., Miller, et al., 1993. *Meth. Enzymol.* 217:581–599. These retroviral vectors have been modified to delete retroviral sequences that are not necessary for packaging of the viral genome and integration into host cell DNA. The GENE SET nucleic acid to be used in gene therapy is cloned into the vector, which facilitates delivery of the gene into a patient. See e.g., Clowes, et al., 1994. *J. Clin. Invest.* 93:644–651; Kiem, et al., 1994. *Blood* 83:1467–1473.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. See e.g., Rosenfeld, et al., 1991 *Science* 252:431–434; Mastrangeli, et al., 1993. *J. Clin. Invest.* 91:225–234. In addition, adeno-associated virus (AAV) has also been proposed for use in gene therapy. See e.g., Walsh, et al., 1993. *Proc. Soc. Exp. Biol. Med.* 204:289–300 (1993).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient. In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, and the like. Numerous techniques are well-known within the art for the introduction of foreign genes into cells (see e.g., Loeffler & Behr, 1993. *Meth. Enzymol.* 217:599–618) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. In a preferred embodiment, epithelial cells are injected (e.g., subcutaneously). In another embodiment, recombinant skin cells may be applied as a skin graft onto the patient. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T-lymphocytes, B-lymphocytes, monocytes, macrophages, neutrophils, eosinophils, megakaryocytes, granulocytes; various stem or progenitor cells, in particular hematopoietic stem or progenitor cells (e.g., as obtained from bone marrow, umbilical cord blood, peripheral blood, fetal liver, and the like). In a preferred embodiment of the present invention, the cell used for gene therapy is autologous to the patient.

In an embodiment in which recombinant cells are used in gene therapy, a mutant GENE SET nucleic acid or nucleic acid encoding a GENE SET anti-sense nucleic acid is introduced into the cells such that it is expressible by the cells or their progeny, and the recombinant cells are then administered in vivo for therapeutic effect. In a specific embodiment, stem or progenitor cells are used. Any stem and/or progenitor cells which can be isolated and maintained in vitro may potentially be used in accordance with this embodiment of the present invention. Such stem cells include but are not limited to hematopoietic stem cells (HSC), stem cells of epithelial tissues such as the skin and the lining of the gut, embryonic heart muscle cells, liver stem cells (see e.g., PCT Publication WO 94/08598) and neural stem cells (see e.g., Stemple & Anderson, 1992. *Cell* 71:973–985).

Epithelial stem cells (ESCs) or keratinocytes can be obtained from tissues such as the skin and the lining of the gut by known procedures. See e.g., Rheinwald, 1980. *Meth. Cell Bio.* 21A:229. In stratified epithelial tissue such as the skin, renewal occurs by mitosis of stem cells within the germinal layer, the layer closest to the basal lamina. ESCs or keratinocytes obtained from the skin or lining of the gut of a patient or donor can be grown in tissue culture. See e.g., Pittelkow & Scott, 1986. *Mayo Clinic Proc.* 61:771. If the ESCs are provided by a donor, a method for suppression of host versus graft reactivity (e.g., irradiation, drug or antibody administration to promote moderate immunosuppression) may also be utilized.

With respect to hematopoietic stem cells (HSC), any technique that provides for the isolation, propagation, and maintenance in vitro of HSC can be used in this embodiment of the invention. Techniques by which this may be accomplished include: (i) the isolation and establishment of HSC cultures from bone marrow cells isolated from the future host, or a donor or (ii) the use of previously established long-term HSC cultures, which may be allogeneic or xenogeneic. Non-autologous HSC are used preferably in conjunction with a method of suppressing transplantation immune reactions of the future host/patient. In a particular embodiment of the present invention, human bone marrow cells can be obtained from the posterior iliac crest by needle aspiration. See e.g., Kodo, et al., 1984. *J. Clin. Invest.* 73:1377–1384. In a preferred embodiment of the present invention, the HSCs can be made highly enriched or in substantially-pure form. This enrichment can be accomplished before, during or after long-term culturing, and can be done by any techniques known in the art. Long-term cultures of bone marrow cells can be established and maintained by using, for example, modified Dexter cell culture techniques (see Dexter, et al., 1977. *J. Cell Physiol.* 91:335) or Witlock-Witte culture techniques (see Witlock & Witte, 1982. *Proc. Natl. Acad. Sci. USA* 79:3608–3612).

In a specific embodiment, the nucleic acid to be introduced for purposes of gene therapy comprises an inducible promoter operably-linked to the coding region, such that expression of the nucleic acid is controllable by controlling the presence or absence of the appropriate inducer of transcription.

(b) Anti-GENE SET Antibodies

In one embodiment of the present invention, as previously discussed hereinabove, antibodies which bind GENE SET proteins or nucleic acids (or derivative, fragments or analogs thereof) are used to treat or prevent hypertension, diabetes, obesity or ischemic stroke. Anti-GENE SET antibodies may also be used in the diagnostic, prognostic and screening methods of the present invention. Such antibodies include, but are not limited to, polyclonal, monoclonal, chimeric, single chain, Fab fragments, and an Fab expression library. In a specific embodiment, antibodies to a human GENE SET protein are produced. In another specific embodiment, antibodies which reduce or inhibit GENE SET activity in vitro and/or in vivo, are provided.

Various procedures known in the art may be used for the production of polyclonal antibodies to an GENE SET protein or derivative or analog. In a particular embodiment, rabbit polyclonal antibodies to an epitope of a GENE SET protein (e.g., the protein of amino acid sequences SEQ ID NOS:1 and 4 or encoded by the nucleotide sequences of SEQ ID NOS:3 and 6, or a subsequence thereof) may be obtained. For the production of antibody, various host animals can be immunized by injection with the native GENE SET protein, a synthetic version, or a derivative or fragment thereof including, but not limited to, rabbits, mice, rats, and the like. Various adjuvants may be used to increase the immunological response, depending on the host species (e.g., Freun's adjuvant).

For preparation of monoclonal antibodies directed toward an GENE SET protein sequence (or derivative or analog thereof) any technique which provides for the production of antibody molecules by continuous in vitro cell lines may be used including, but not limited to: the hybridoma technique (see Kohler & Milstein, 1975. *Nature* 256:495–497); the trioma technique; the human B-cell hybridoma technique (see Kozbor, 1983. et al., *Immunology Today* 4:72) and the EBV-hybridoma technique to produce human monoclonal antibodies (see Cole, et al., *Monoclonal Antibodies and Cancer Therapy* (Alan R. Liss, Inc., New York, N.Y.). In an additional embodiment of the invention, monoclonal antibodies can be produced in germ-free animals utilizing recent technology (see e.g., PCT Publication US90/02545). Human antibodies are within the scope of the present invention and may be obtained by using human hybridomas (see e.g., Cote, et al., 1983. *Proc. Natl. Acad. Sci. U.S.A.* 80:2026–2030) or by transforming human B-cells with Epstein-Barr virus (EBV) in vitro (see e.g., Cole, et al., 1985. *Monoclonal Antibodies and Cancer Therapy* (Alan R. Liss, New York, N.Y.). Additionally within the scope of the present invention are the production of "chimeric antibodies" (see e.g., Morrison, et al., 1984. *Proc. Natl. Acad. Sci. U.S.A.* 81:6851–6855) which may be produced by splicing the genes from a mouse antibody molecule specific for GENE SET together with genes from a human antibody molecule of appropriate biological activity.

In one embodiment of the present invention, single chain antibodies (see U.S. Pat. No. 4,946,778) may be adapted to produce GENE SET-specific single chain antibodies. An additional embodiment of the invention discloses the utilization of Fab expression libraries (see e.g., Huse, et al., 1989. *Science* 246:1275–1281) so as to allow rapid and easy identification of monoclonal Fab fragments with the desired specificity for GENE SET proteins (or derivatives or analogs thereof).

Antibody fragments which contain the idiotype of the molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, the Fab fragments which can be generated by treating the antibody molecule with papain and a reducing agent, and Fv fragments.

In the production of antibodies, screening for the desired antibody may be accomplished by techniques known in the art (e.g., enzyme-linked immunosorbent assay(ELISA)). In a specific embodiment, the selection of antibodies which recognize a specific portion of an GENE SET protein may be accomplished by an assay which utilize hybridomas specific for a product which binds to a GENE SET fragment containing such portion. For selection of an antibody which possesses the ability to reduce or inhibit GENE SET activity, one may screen the antibody in any of the assays for GENE SET activity described infra.

(c) Anti-Sense GENE SET Nucleic Acids

In a specific embodiment of the present invention, the function of GENE SET protein(s) is reduced or inhibited by GENE SET anti-sense nucleic acids, utilized to treat or prevent stroke, hypertension, diabetes or obesity. The present invention provides the therapeutic or prophylactic use of nucleic acids of at least six nucleotides which are anti-sense to a gene or cDNA encoding GENE SET or a portion thereof. An GENE SET "anti-sense" nucleic acid, as utilized herein, refers to a nucleic acid species which is capable of hybridizing to a portion of an GENE SET RNA (preferably MRNA) by virtue of sequence complementarily. The anti-sense nucleic acid may be complementary to a coding and/or noncoding region of an GENE SET MRNA. Such anti-sense nucleic acids have utility as Therapeutics that reduce or inhibit GENE SET function, and can be used in the treatment or prevention of disorders as described, supra.

The GENE SET anti-sense nucleic acids are of at least six nucleotides and are preferably oligonucleotides (ranging from 6–150 nucleotides or, more preferably, 6–50 nucleotides). In specific aspects, the oligonucleotide is at least 10 nucleotides, at least 15 nucleotides, at least 100 nucleotides, or at least 125 nucleotides. The oligonucleotides may be DNA, RNA or chimeric mixtures (or derivatives or modified versions thereof) and may be single-stranded or double-stranded. The oligonucleotide can be modified at the base moiety, sugar moiety, or phosphate backbone. The oligonucleotide may include other appending groups such as peptides, or agents facilitating transport across the cell membrane (see e.g., Letsinger, et al., 1989. *Proc. Natl. Acad. Sci. U.S.A.* 86:6553–6556) or blood-brain barrier (see e.g., PCT Publication No. WO 89/10134); hybridization-triggered cleavage agents (see e.g., Krol, et al., 1988. *BioTechniques* 6:958–976) or intercalating agents (see e.g., Zon, 1988. *Pharm. Res.* 5:539–549).

The GENE SET anti-sense nucleic acid of the present invention is preferably an oligonucleotide and more preferably, a single-stranded DNA. In a preferred embodiment, the oligonucleotide comprises a sequence anti-sense to a portion of human GENE SET. The oligonucleotide may be modified at any position on its structure with substituents generally known within the art.

Oligonucleotides of the invention may be synthesized by standard methods known within the art, for example, by use of an automated DNA synthesizer (e.g., Biosearch, Applied Biosystems, etc). As an example, but of limitation, phosphorothioate oligonucleotides may be synthesized by the method of Stein, et al. (1988. *Nucl. Acids Res.* 16:3209); methylphosphonate oligonucleotides may be prepared by use of controlled pore glass polymer supports (see e.g., Sarin, et al., 1988. *Proc. Natl. Acad. Sci. U.S.A.* 85:7448–7451) and similar synthesis methodologies.

In a specific embodiment of the present invention, the GENE SET anti-sense oligonucleotide comprises catalytic RNA or a ribozyme (see e.g., PCT International Publication WO 90/11364; Sarver, et al., 1990. *Science* 247:1222–1225). In another specific embodiment, the oligonucleotide is a 2N-0-methylribonucleotide (see e.g., Inoue, et al., 1987. *Nuc. Acids Res.* 15:6131–6148) or a chimeric RNA-DNA analogue (see e.g., Inoue, et al., 1987. *FEBS Lett.* 215:327–330).

In another embodiment, the GENE SET anti-sense nucleic acid of the present invention is produced intracellularly by in vivo transcription from an exogenous sequence. For example, a vector may be introduced in vivo such that the vector (or a portion thereof) is transcribed, producing an anti-sense nucleic acid (RNA) of the present invention. Such a vector would contain a sequence encoding the GENE SET anti-sense nucleic acid, and can remain episomal or become chromosomally-integrated, so long as it can be transcribed to produce the desired anti-sense RNA. The aforementioned vectors may be comprised of plasmid, viral, or others known in the art which are utilized for replication and expression in mammalian cells and may be constructed by recombinant DNA technology methodologies standard within the art. Expression of the sequence encoding the GENE SET anti-sense RNA may be by any promoter known in the art to act in mammalian, preferably human, cells. Such promoters can be inducible or constitutive and include, but are not limited to: (i) the SV40 early promoter region (see e.g., Bernoist & Charnbon, 1981. *Nature* 290:304–310); (ii) the promoter contained in the 3'-terminus long terminal repeat (LTR) of Rous sarcoma virus (see e.g., Yamamoto, et al., 1980. *Cell* 22:787–797); (iii) the Herpesvirus thymidine kinase promoter (see e.g., Wagner, et al., 1981. *Proc. Natl. Acad. Sci. U.S.A.* 78:1441–1445); (iv) the regulatory sequences of the metallothionein gene (see e.g., Brinster, et al., 1982. *Nature* 296:39–42), and the like.

The anti-sense nucleic acids of the present invention comprise a sequence complementary to at least a portion of an RNA transcript of an GENE SET gene, preferably a human GENE SET gene. However, absolute complementarily, although preferred, is not a requirement. A sequence "complementary to at least a portion of an RNA," as utilized herein refers to a sequence possessing sufficient complementarily to be able to hybridize with the RNA, forming a stable duplex; in the case of double-stranded GENE SET anti-sense nucleic acids. Similarly, a single strand of the duplex DNA or triplex formation may be assayed in a similar manner. The ability to hybridize will dependent upon both the degree of complementarily and the length of the anti-sense nucleic acid. Generally, the longer the hybridizing nucleic acid, the more base mismatches with a an GENE SET RNA it may contain and still form a stable duplex (or triplex, as the case may be). One skilled in the art may ascertain a tolerable degree of mismatch by use of standard procedures to determine the melting point of the hybridized complex.

The invention further provides pharmaceutical compositions (i.e., "Therapeutics") comprising an effective amount of the GENE SET anti-sense nucleic acids of the present invention within a pharmaceutically acceptable carrier. In a specific embodiment, pharmaceutical compositions comprising GENE SET anti-sense nucleic acids may be administered via liposomes, microparticles, or microcapsules. It may be useful to use such compositions to achieve sustained release of the GENE SET anti-sense nucleic acids.

The amount of GENE SET anti-sense nucleic acid which will be effective in the treatment or prevention of ischemic disease will depend on the nature of the disease, and can be determined by standard clinical techniques. Where possible, it is desirable to determine the anti-sense cytotoxicity in cells in vitro, and then in useful animal model systems prior to testing and use in humans.

(4) Methods of Diagnosis, Prognosis and Screening

The present invention also discloses methodologies which relate to the diagnosis, prognosis and screening of stroke, hypertension, diabetes and/or obesity.

In one embodiment, anti-GENE SET-antibodies are used to detect and quantitate mutant GENE SET levels in one or more tissues (e.g., blood) of a subject by use of an immunoassay-based methodology. Specifically, such an immunoassay is performed by contacting a sample derived from a patient with an anti-GENE SET antibody under conditions such that immunospecific-binding can occur, and detecting or measuring the amount of any immunospecific-binding by the antibody. It should be noted, however, that the particular amino acid deletion, insertion or substitution within the amino acid sequence of the mutant GENE SET protein can change the epitope recognized by a specific anti-(wild-type) GENE SET antibody, such that antibody may bind the mutant GENE SET protein to a lesser extent, or not at all. Additionally, antibodies may be generated against the mutant GENE SET protein, or portion thereof, which bind specifically to the particular mutant GENE SET, but not the wild-type GENE SET (as determined by the in vitro immunoassay methodology described infra). These specific anti-mutant GENE SET antibodies may be used to detect the presence of GENE SET by measuring the immunospecific-binding by the anti-mutant GENE SET antibodies and, optionally, the lack of immunospecific-binding by the anti-(wild-type) GENE SET antibodies. Moreover, GENE SET proteins possessing deletion or insertion mutations may be detected by either an increase or decrease in protein size by methodologies which include, but are not limited to, for example, but not limited to, Western blot analysis using an anti-GENE SET antibody which recognizes both the mutant and wild-type GENE SET.

Immunoassays which may be utilized in the practice of the present invention include, but are not limited to, competitive and non-competitive assay systems using techniques such as Western blots, radioimmunoassays (RIAs), enzyme-linked immunosorbent assays(ELISA), "sandwich" immunoassays, immunoprecipitation assays, precipitation reactions, gel diffusion precipitin reactions, immunodiffusion assays, agglutination assays, complement-fixation assays, immunoradiometric assays, fluorescent immunoassays, protein-A immunoassays, and the like.

In a specific embodiment of the present invention, methods of diagnosis, prognosis and screening are disclosed and utilize the detection of mutant GENE SET alleles in genomic DNA or mRNA (i.e., genetic screening). These aforementioned mutant GENE SET alleles may be detected by any method known in the art for detecting mutations in genomic DNA including, but not limited to: DNA hybridization methods (e.g. Southern Blotting), RFLP mapping, PCR-based amplification methodologies, and the like, may be used with nucleic acid probes which are complementary to both the mutation and the corresponding position within the wild-type GENE SET sequence.

In a preferred embodiment, allele-specific PCR (ASP) may be used to detect mutant GENE SET alleles. In the ASP methodology, a target DNA is, preferentially, amplified only if it is completely complementary to the 3'-terminus of a specific PCR amplification primer. The 3'-terminus of the primer is designed so as to terminate at, or within one or two nucleotides of a known mutation site within the GENE SET gene (target DNA) to which it possesses a complementary sequence. Under the appropriate reaction conditions, the target DNA is not amplified if there is a single nucleotide mismatch (e.g., a nucleotide substitution caused by a mutation) or a small deletion or insertion, at the 3'-terminus of the primer. See e.g., Okayama, et al., 1989. *J. Lab. Clin. Med.* 114:105–113; Sommer, et al., 1992. *BioTechniques* 12:82–87). Accordingly, ASP may be utilized to detect either the presence or absence of (at least) a single nucleotide mismatch between the primer sequence (which is complementary to the pre-selected GENE SET target sequence) and a nucleic acid within the sample. Amplification of the GENE SET sequence is indicative of a lack of even a single mismatched nucleotide.

Additionally, where the mutant comprises a deletion or insertion mutation, mutant GENE SET alleles may be detected by screening for an increase or decrease in the length of the GENE SET nucleic acid sequence, or portion thereof. The increase or decrease in length may be detected by any method known within the art for measuring the length of nucleic acids, including, but not limited to, amplification of a specific fragment of the GENE SET sequence from the subject to be diagnosed or screened and from a standard or control sample and comparison of the length of the fragments by any size fractionation method (e.g., denaturing polyacrylamide gel electrophoresis.

Additionally, kits for diagnostic or screening use are also disclosed herein which comprise, in one or more containers, an anti-GENE SET antibody or anti-GENE SET mutant antibody and, optionally, a labeled binding partner to the antibody. Alternatively, the anti-GENE SET antibody or anti-GENE SET mutant antibody may be detectably-labeled (e.g., with a chemiluminescent, enzymatic, fluorescent, or radioactive moiety). In another embodiment, a kit is provided which comprises, in one or more containers, a nucleic acid probe which is capable of specifically-hybridizing to GENE SET RNA or, preferably, to mutant GENE SET RNA. In a specific embodiment of the present invention, a kit is provided which comprises, in one or more containers, a pair of primers (e.g., each in the size range of 6–30 nucleotides) which are capable of priming amplification reactions, under appropriate reaction conditions, of at least a portion of a GENE SET nucleic acid. These amplification reactions include, but are not limited to, polymerase chain reaction (PCR); ligase chain reaction; Qβ replicase, cyclic probe reaction or other amplification methods known within the art. A kit may, optionally, further comprise, in a container, a predetermined concentration of a purified GENE SET protein or nucleic acid, for use as a standard or control.

(5) Assays for Modulators of GENE SET Proteins and Nucleic Acids

A variety of methodologies are available within the art for assaying the activity of GENE SET proteins (and derivatives, analogs, fragments and homologs of GENE SET proteins), as well as for the nucleic acids encoding the GENE SET proteins (and derivatives, analogs, fragments and homologs thereof). Methods are also available for the screening of putative GENE SET modulators (e.g., GENE SET agonists, antagonists and inhibitors). Such modulators of GENE SET activity include, but are not limited to, GENE SET anti-sense nucleic acids, anti-GENE SET antibodies, and competitive inhibitors of GENE SET proteins for binding to the GENE SET protein receptors.

The activity of the GENE SET proteins (and derivatives, fragments, analogs and homologs of GENE SET proteins), the nucleic acids encoding these GENE SET proteins (and derivatives, fragments, analogs and homologs thereof) and putative modulators of GENE SET protein activity may also be ascertained in vivo. For example, infusion of GENE SET proteins in humans causes significant increases in cGMP levels in plasma and urine. See e.g. Vesely, et al., 1995. *Am. J. Med. Sci.* 310:143–149; Vesely, et al., 1996. *Metabolism: Clin. & Exp.* 45:315–319. Administration of GENE SET proteins to humans also elicits significant diuresis and reduction in blood pressure (see e.g., Vesely, et al., 1996. *Life Sciences* 59:243–254); similar effects have also been observed in rodents (see e.g., Garcia, et al., 1989. *Hypertension* 13:567–574). In accord, the mutant GENE SET proteins and nucleic acids (and derivatives, analogs, fragments and homologs thereof) and putative GENE SET modulators may be assayed by the administration of a "test compound" to an animal, preferably a non-human test animal, followed by the measurement of the one or more of the physiological parameters described above (e.g., cGMP levels in urine and/or plasma, diuretic effect, decrease in blood pressure, and the like).

Another embodiment of the present invention discloses a methodology for screening a GENE SET mutant for a change in activity comprising (i) administering the GENE SET mutant to a test animal prone to stroke, hypertension, diabetes or obesity and (ii) measuring of stroke latency within the test animal in which stroke latency is indicative of GENE SET activity. In a specific embodiment, a recombinant test animal, which expresses a GENE SET transgene or expresses a member of the GENE SET under the control of a promoter which is not the native GENE SET gene promoter at an increased level relative to a wild-type test animal, is used to screen the GENE SET for a change in GENE SET activity.

In another embodiment of the present invention, a method for screening for a modulator of GENE SET activity, or of latency or predisposition to stroke, is provided which comprises measuring stroke latency within a stroke-prone animal that recombinantly expresses a putative modulator of GENE SET activity, in which a change in stroke latency relative to an analogous stroke-prone animal which does not recombinantly-express the putative modulator, indicates that the putative modulator possesses the ability to modulate GENE SET activity, or latency or predisposition to stroke.

In yet another embodiment, a method is provided for screening an GENE SET mutant for an effect on latency or predisposition to stroke comprising measuring stroke latency within a stroke-prone animal which recombinantly-expresses a GENE SET mutant, in which a change in stroke latency relative to an analogous stroke-prone animal which does not recombinantly express the GENE SET mutant indicates that the GENE SET mutant has an effect on latency or predisposition to stroke, hypertension, diabetes or obesity. In a preferred embodiment, a GENE SET mutant is screened for an increase in stroke latency or a decrease in predisposition to stroke.

(6) Pharmaceutical Compositions and Therapeutics

The present invention discloses methods of treatment and prophylaxis by administering to a subject of an effective amount of a Therapeutic of the invention. In a preferred embodiment, the Therapeutic is substantially-purified. The subject is preferably an animal which, preferably, is a mammal and most preferably human.

Formulations and methods of administration which may be employed when the Therapeutic comprises a nucleic acid are described in Sections 3(a) and 3( c), supra; whereas additional appropriate formulations and routes of administration may be selected from among those described infra.

Numerous types of pharmaceutical composition delivery systems are well-known within the art and may be utilized to administer a Therapeutic of present the invention. These aforementioned delivery systems include, but are not limited to: (i) encapsulation in liposomes, microparticles and microcapsules; (ii) recombinant cells capable of expressing the Therapeutic; (iii) receptor-mediated endocytosis (see e.g., Wu & Wu, 1987. *J. Biol. Chem.* 262:4429–4432); (iv) construction of a Therapeutic nucleic acid as part of a retroviral or other vector, and the like. Methods of administration/introduction include, but are not limited to, intradermal, intramuscular, intraperitoneal, intravenous, subcutaneous, intranasal, epidural, and oral routes. The Therapeutic may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the Therapeutic of the present invention into the central nervous system by any suitable route (e.g., intraventricular and intrathecal injection). Intraventricular injection may be facilitated by the use of an intraventricular catheter, for example, attached to a reservoir, such as an Ommaya reservoir. Pulmonary administration may also be employed (e.g., by use of an inhaler or nebulizer) and formulation with an aerosolizing agent.

In a specific embodiment of the present invention, it may be desirable to administer the Therapeutic of the present invention locally to the area in need of treatment; this may be achieved by, for example, and not by way of limitation, local infusion during surgery, topical application (e.g., in conjunction with a wound dressing after surgery), by injection, by means of a catheter, by means of a suppository, or by means of an implant, said implant being of a porous, non-porous, or gelatinous material, including membranes, such as sialastic membranes, or fibers.

In another specific embodiment of the present invention, the Therapeutic may be delivered in a vesicle, in particular a liposome. See e.g., Langer, 1990. *Science* 249:1527–1533. In yet another specific embodiment, the Therapeutic may be delivered via a controlled release system including, but not limited to: a pump (see e.g., Sefton, 1987. *CRC Crit. Ref. Biomed. Eng.* 14:201) and polymeric materials (see e.g., Smolen & Ball, 1983. *Controlled Drug Bioavailability, Drug Product Design and Performance* (Wiley, New York, N.Y.). In addition, a controlled release system may be placed in proximity of the therapeutic target (e.g., the brain), thus requiring only a fraction of the total systemic dose. See e.g., Goodson, 1984. *Medical Applications of Controlled Release,* (Wiley, New York, N.Y.).

In a specific embodiment of the present invention where the Therapeutic is a nucleic acid encoding a protein-based Therapeutic, the nucleic acid may be administered in vivo to promote expression of its encoded protein, by constructing of the aforementioned protein as part of an appropriate nucleic acid expression vector, and administering the construct so that it becomes intracellular by methodologies which include, but are not limited to: (i) use of a retroviral vector (see e.g., U.S. Pat. No. 4,980,286); (ii) use direct injection; (iii) use of microparticle bombardment (e.g., a gene gun; Biolistic, DuPont); (iv) coating with lipids or cell-surface receptors or transfecting agents; (v) administering it in linkage to a homeobox-like peptide which is known to enter the nucleus (see e.g., Joliot, et al., 1991. *Proc. Natl. Acad. Sci. USA* 88:1864–1868) and the like.

In an alternate embodiment of the present invention, a nucleic acid-based Therapeutic may be introduced intracellularly and incorporated by homologous recombination within host cell DNA for expression.

The present invention also discloses pharmaceutical compositions. Such compositions comprise a therapeutically-effective amount of a Therapeutic within a pharmaceutically-acceptable carrier. In a specific embodiment, the term "pharmaceutically acceptable," as utilized herein, is defined as the composition being approved by a regulatory agency of the Federal or a state government or listed in the U.S. Pharmacopeia or other generally recognized pharmacopeia for use in animals and, more particularly, in humans. The term "carrier," as utilized herein, refers to a diluent, adjuvant, excipient, or vehicle with which the therapeutic is administered. Such pharmaceutical carriers include, but are not limited to: sterile liquids (e.g., water, physiological saline and the like) and oils (e.g., oils of petroleum, animal, vegetable or synthetic origin, such as peanut oil, soybean oil, mineral oil, sesame oil and the like). Water is a preferred carrier when the pharmaceutical composition is administered intravenously. Additionally, saline solutions and aqueous dextrose and glycerol solutions may also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Martin, 1965. *Remington's Pharmaceutical Sciences*. Such compositions will contain a therapeutically-effective amount of the Therapeutic, preferably in purified form and, most preferably, in a substantially-purified form, together with a suitable amount of carrier so as to provide the form for proper administration to the patient. The formulation should be suited to the mode of administration.

In a preferred embodiment of the present invention, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The Therapeutics of the present invention may be formulated with pharmaceutically-acceptable salts including those derived from hydrochloric, phosphoric, acetic, etc., and those formed with free carboxyl groups such as those derived from sodium, potassium, calcium, ferric hydroxides, isopropylamine, triethylamine, 2-ethylamino ethanol, histidine, procaine, etc.

The amount of the Therapeutic of the present invention which will be effective in the treatment of a particular disorder or condition will be dependent upon the exact nature of the disorder or condition, and can be quantitatively-determined by standard clinical techniques. In addition, in vitro assays may (optionally) be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20–500 $\mu$g of active compound per kilogram (kg) body weight. Suitable dosage ranges for intranasal administration are generally about 0.01 pg/kg body weight to 1 mg/kg body weight. Effective doses may be extrapolated from dose-response curves derived from in vitro or animal model test systems. Suppositories generally contain active ingredient in the range of 0.5% to 10% by weight; oral formulations preferably contain 10% to 95% active ingredient.

The present invention also provides a pharmaceutical pack or kit comprising one or more containers filled with one or more of the ingredients of the pharmaceutical compositions of the invention. Optionally associated with such container(s), a notice in the form prescribed by a governmental agency regulating the manufacture, use or sale of pharmaceuticals or biological products, which notice reflects approval by the agency of manufacture, use or sale for human administration.

(7) Animal Models

The present invention discloses animal models. In one embodiment, animal models for stroke, hypertension, diabetes or obesity are provided. Transgenic animals may be bred or produced through molecular-biological means, which over-express or under-express one or more of the GENE SET genes (e.g., by introducing a member or members of the GENE SET gene under the control of a heterologous promoter or a promoter which facilitates the expression of GENE SET proteins and/or nucleic acids in tissues which do not normally express GENE SET components. Additionally, "knockout" mice may be initially produced by promoting homologous recombination between a GENE SET gene in its chromosome and an exogenous GENE SET gene that has been rendered biologically inactive, preferably by insertion of a heterologous sequence (e.g., an antibiotic resistance gene) or by non-homologous recombination.

In a preferred embodiment of the present invention, introduction of heterologous DNA is carried out by transforming embryo-derived stem (ES) cells with a vector containing the insertionally-inactivated GENE SET gene or a GENE SET gene which is under the control of a heterologous promoter, followed by injecting the ES cells into a blastocyst and implanting the blastocyst into a "foster mother" animal. Accordingly, the resulting mice are chimeric animals ("knockout animal" or "transgenic animal") in which an GENE SET gene has been inactivated or overexpressed or misexpressed (see e.g., Capecchi, 1989. *Science* 244:1288–1292). The chimeric animal can then be bred to produce additional knockout or transgenic animals. Such chimeric/transgenic animals include, but are not limited to, mice, hamsters, sheep, pigs, cattle, etc., and are, preferably, non-human mammals. Transgenic and knockout animals can also be made in *D. melanogaster, C. elegans,* and the like, by methods which are commonly-known within the art.

Another embodiment of the present invention provides a recombinant non-human animal containing a mutant GENE SET gene, under the control of a promoter which is not the native GENE SET gene promoter, in which the mutant GENE SET gene encodes a mutant GENE SET which increases latency to stroke. Yet another embodiment discloses a recombinant non-human animal that is the product of a process comprising introducing a nucleic acid into the non-human animal, or an ancestor thereof, said nucleic acid comprising a mutant GENE SET gene sequence.

(8) Specific Examples

Heart, brain, fat, liver and kidney tissue from spontaneously hypertensive rats (SHR), stroke-prone SHR (SHR-SP) and control Wistar Kyoto rats (WKY) were analyzed by the GeneCalling® methodology (see PCT Publication WO 97/15690) to facilitate the identification and characterization of genes which are differentially-expressed in the SHR and SHR-SP rats, as compared to the control WKY animals.

(A) Materials and Methodologies (i) Isolation of Total Cellular RNA and Poly(A)$^+$ rRNA SHR, SHR-SP and WKY rats were maintained on normal rat chow (Purina) and water ad libitum. Thirteen week old rats were sacrificed and the hearts, liver, fat, kidney and brain tissues were removed and quick-frozen in liquid nitrogen immediately following dissection. The whole organs were stored at −70° C. for subsequent processing.

Total cellular RNA was extracted from 5 mg of heart, liver, fat, kidney, or brain tissue by initially grinding the tissue into a fine powder in liquid nitrogen. The powdered tissue was then transferred to a tube containing 500 $\mu$l Triazol Reagents (Life Technologies; Gaithersburg, Md.) and was dispersed in the Triazol Reagent® using a Polytron homogenizer (Brinkman Instruments; Westbury, N.Y.). See e.g., Chomszynski, et al. 1987. *Annal. Biochem.* 162 156–159; Chomszynski, et al., 1993. *BioTechniques* 15:532–533, 536–537. The total cellular RNA fraction was then extracted with 50 $\mu$l BCP (1-bromo-3-chloropropane; Molecular Research; Cincinnati, Ohio) to facilitate phase separation. The extraction mixture was centrifuged for 15 minutes at 4° C. at 12,000×G, and the aqueous phase was removed and transferred to a fresh tube. The RNA was then precipitated with 0.5 volume of isopropanol per original volume of Triazol Reagents used, and the sample was re-centrifuged at room temperature for 10 minutes at 12,000×G. The supernatant was then discarded, the pellet washed with 70% ethanol and re-centrifuged at room temperature for 5 minutes at 12,000×G. Finally the 70% ethanol was removed and the centrifuge tube was inverted and let stand to dry in this position. The resulting RNA pellet was re-suspended in 100 $\mu$l water (i.e., 1 $\mu$l/mg of original tissue weight) and heated to 55° C. until completely dissolved. The final concentration of total cellular RNA was quantitated by fluorometry with OliGreen® (Molecular Probes; Eugene, Oreg.). In addition, the quality of the total cellular RNA was determined by both spectrophotometry and formaldehyde agarose gel electrophoresis.

Poly(A)$^+$ RNA was prepared from 100 $\mu$g of total cellular RNA by use of affinity chromatography with oligo(dT) magnetic beads (PerSeptive; Cambridge, Mass.) or with the Dynabeads mRNA Direct Kit® (Dynal; Oslo, Norway) as directed by the manufacturer. The Poly(A)$^+$ RNA was harvested in a small volume of sterile water, and the final yield quantified by OD$_{260}$ measurement and fluorometry with OliGreen® (Molecular Probes; Eugene, OR). The Poly(A)$^+$ RNA was stored at −20° C. for subsequent utilization in cDNA synthesis and GeneCalling® protocols.

(ii) cDNA Synthesis

Prior to cDNA synthesis, each of the Poly(A)+RNA samples from the aforementioned tissues were treated with DNase to remove endogenous, contaminating DNA. 28$\mu$l of 5×reverse transcriptase buffer (Life Technologies; Gaithersburg, Md.), 10 $\mu$l 0.1 M DTT, 5 units RNAguard® (Pharmnacia Biotech, Upsala, Sweden) per 100 mg tissue and 1 unit RNase-free DNase I (Pharmacia Biotech) per 100 mg tissue, were added to the re-suspended RNA samples. The reaction mixtures were then incubated at 37° C. for 20 minutes. The total RNA concentration was quantified by measuring OD$_{260}$ of a 100-fold dilution and the samples were stored at −20° C.

cDNA was synthesized from the Poly(A)$^+$ RNA as follows: the Poly(A)$^+$ RNA isolated from each of the aforementioned tissues was mixed with 50 ng random hexamer primers (50 ng/$\mu$l) in 10 $\mu$l of water. The mixtures were heated to 70° C. for 10 minutes, quick-chilled in an ice-water slurry, and kept on ice for 1–2 min. The condensates were then collected by centrifugation in a microfuge for approximately 10 seconds.

The first-strand synthesis was performed by adding to the reaction mixtures: 4 $\mu$l 5×first-strand buffer (from a BRL cDNA Synthesis Kit; Grand Island, N.Y.), 2 $\mu$l 100 mM DTT, 1 $\mu$l 10 mM dNTP mix, and 2 $\mu$l water to each of the primer-annealed Poly(A)$^+$ RNA. Alternately, 200 pmols of oligo(dT)$_{25}$V (V=A, C or G) was utilized as a primer in the first-strand synthesis reactions. The reaction mixtures were then incubated at 37° C. for 2 minuets, followed by the addition of 1 $\mu$l of Superscript II® reverse transcriptase (BRL) and the reactions were incubated at 37° C. for 1 hour.

Second-strand cDNA synthesis was then performed. The samples were placed on ice and to each of the first-strand reaction mixture was added: 30 $\mu$l of 5×second-strand buffer, 90 $\mu$l of cold water, 3 $\mu$l of 10 mM dNTP, 1 $\mu$L (10 units) of *E. coli* DNA ligase (BRL), 4 $\mu$l (40 units) of *E. coli* DNA polymerase I (BRL), and 1 $\mu$l (3.5 units) of *E. coli* RNaseH (BRL) and the reaction mixtures were incubated for 2 hours at 16° C. The resulting double-stranded cDNA was then incubated with 2 $\mu$l of T$_4$ DNA polymerase (5 units) at 16° C. for 5 minuets.

The resulting cDNA was then dephosphorylated with Arctic Shrimp Alkaline Phosphatase ("SAP"; USB; St. Louis, Mich.) by adding to each reaction mixture: 20 $\mu$l 10×SAP buffer, 25 $\mu$l of water, and 5 $\mu$l (5 units) of SAP. The reactions were incubated at 37° C. for 30 minutes.

The cDNA was extracted with phenol/chloroform (50:50 v/v), chloroform/isoamyl alcohol (99:1 v/v) and precipitated from the aqueous phase by the addition of NaOAc pH 5.0 to 0.3 M, 20 $\mu$g glycogen, and 2.5 volumes of ethanol followed by incubation at −20° C. for 10 minuets. The cDNA was collected by centrifugation at 14,000×g for 10 minuets. The supernatant was then aspirated and the resulting cDNA pellet was washed with 75% ethanol, resuspended in TE buffer (pH 7.0) and the yield of CDNA was estimated using fluorometry with Picogreen® (Molecular Probes; Eugene, Oreg.).

(iii) GeneCalling® Methodology

The GeneCalling® methodology is comprised of a 3-step process which involves cDNA fragmentation, tagging and amplification. Fragmentation was achieved by restriction enzyme digestions in a 50 $\mu$l reaction mix containing 5 units of each restriction enzyme, 1 ng of double-stranded cDNA and 5 $\mu$l of the appropriate 10×restriction endonuclease buffer. Analysis of all mRNAs was achieved by performing 80 separate sets of cDNA fragmentation reactions, each with a different pair of restriction enzymes. Tagging was achieved by ligation of amplification cassettes with ends compatible to the 5'- and 3-termini of the cDNA fragments. A FAM label was incorporated onto the 5'-terminus of one of the PCR primers. Incubation of the ligation reaction was performed at 16° C. for 1 hour in 10 mM ATP, 2.5% PEG, 10 units T4 DNA ligase and 1×ligase buffer.

PCR amplification was performed by the addition of the following reagents to each of the reaction tubes: 2 μl 10 mM dNTP, 5 μl 10×TB buffer (500 mM Tris, 160 mM $(NH_4)_2SO_4$, 20 mM $MgCl_2$, pH 9.15), 0.25 μl KlenTaq® (Clontech Advantage):PFU® (Stratagene, La Jolla Calif.) (16:1) and 32.75 μl $H_2O$. Twenty (20) cycles of amplification (30 seconds at 96° C., 1 minute at 57° C., 2 minutes at 72° C.), followed by 10 minutes at 72° C., were performed in a PTC-100 Thermal Cycler equipped with a mechanized lid (MJ Research; Watertown, Mass.).

Post-PCR amplification product purification was performed using streptavidin magnetic beads (MPG® Beads; CPG, Lincoln Park, N.J.). After washing the beads twice with buffer 1 (3 M NaCl, 10 mM Tris-HCl, 1 mM EDTA, pH 7.5), 20 μl of buffer 1 was mixed with the PCR product for 10 minutes at room temperature, separated with a magnet, and washed once with buffer 2 (10 mM Tris, 1 mM EDTA, pH 8.0). The beads were then dried and resuspended in 3 μl of buffer 3 (80% (v/v) formamide, 4 mM EDTA, 5% TAMRA- or ROX-tagged molecular size standard (PE-Applied Biosystems, Foster City Calif.). Following denaturation at 96° C. for 3 minutes, samples were then loaded onto 5% polyacrylamide, 6M urea, 0.5×TBE ultrathin gels and electrophoresed on a proprietary Niagara® gel electrophoresis system. PCR products were visualized by virtue of the fluorescent FAM label at the 5' end of one of the PCR primers, which ensures that all detected fragments have been digested by both enzymes.

The primary components of the Niagara® gel electrophoresis system are an interchangeable horizontal ultrathin gel cassette mounted in a platform employing stationary laser excitation and a multi-color CCD imaging system. Each gel cassette may be loaded with a total of 48 lanes (4 cycles of 12 wide) directly from a 96-well plate using a Beckman Biomek 2000® robotic arm (Beckman, Sunnyvale, Calif.). The Niagara electrophoresis system has the advantage of high throughput, with separation of fragments between 30 and 450 bases in 45 minutes.

(iv) Niagarae Gel Interpretation

The output from the Niagara® gel electrophoresis system was processed using the Java-based, internet-ready Open Genome Initiative (OGI) software suite. Gels images were initially visually checked and tracked. Each lane contained the FAM-labeled products of a single GeneCalling® reaction plus a molecular weight "sizing-ladder" spanning the range from 50 to 500 bp. The ladder peaks provided a correlation between camera frames (collected at 1 Hz) and DNA fragment size in base pairs (bp). Following tracking, the lanes were extracted and the peaks in the sizing ladder were ascertained. Linear interpolation between the ladder peaks was utilized to convert the fluorescence traces from frames to base pairs. A final quality control (QC) step checked for various anomalies (e.g., low signal-to-noise ratio, poor peak resolution, missing ladder peaks, and lane-to-lane sample bleeding). Data which passed all of the aforementioned criteria were submitted as point-by-point length versus amplitude addresses to an Oracle 8 database for subsequent difference identification.

(v) Difference Identification

For each restriction enzyme pair (subsequence) comprising each sample set, a composite trace was calculated. This composite trace calculation entailed compiling all of the individual sample replicates, followed by application of a scaling algorithm for best-fit to normalize the traces of the experimental set versus that of the control set. The scaled traces were then compared on a point-by-point basis to define areas of amplitude difference which meet the minimum, pre-specified threshold for a statistically-significant difference. Once a region of difference was characterized, the local maximum for the corresponding traces of each set was identified. All difference peaks were stored as unique database addresses in the specified expression difference analysis.

(vi) Northern Blot Analysis

1 μg of Poly (A)$^+$ RNA from 3 animals of each genotype was electrophoresed in agarose/formaldehyde gels, blotted to PVD-nylon filters and probed with fill-in oligonucleotides labeled with $^{32}$P-dCTP. The hybridization was quantitated with a storage phosphor imaging plate using the Fuji BAS2000®. Blots were stripped and re-probed for GAPDH to normalize gene expression levels. Induction levels are expressed as the ratio of average normalized hybridization signals.

(vii) Radiation Hybrid Mapping

A commercially-available, rat T55 radiation hybrid panel (Research Genetics; Huntsville, Ala.), consisting of 106 individual hybrids was utilized in this analysis. It was determined empirically, that hybrid samples 1, 20, 35, 38, 60 and 90 had very low retention when compared to the other samples in the panel. In addition, a total of 94 rat hybrid (RH) samples was utilized, in order to efficiently perform PCR in a 96-well format (94 RH samples, plus negative and positive control). Accordingly, RH samples 1–100 from the T55 radiation hybrid panel, excluding the 6 low retention RH samples, previously discussed.

MapPairs® simple sequence repeat (SSR) markers (Research Genetics) were utilized. All markers were run in duplicate and evaluated/scored as a pair. RH templates were distributed into 384 well PCR plates (MJ Research) at 20 ng/well using a Tecan Genesis 100® pipetting robot, and allowed to desiccate. PCR reactions were performed in 5 μl total volumes using the following concentrations of reagents: .5 μM each primer, 200 μM dNTPs, 1×PC2 buffer (50 mM Tris-HCl pH 9.1, 16 mM ammonium sulfate, 3.5 mM $MgCl_2$, 150 μg/ml BSA, 1×Rediload (Research Genetics) and 0.25U KlenTaq® (Clonetech Advantage). PCR amplification reaction conditions (Thermocycle) were as follows: initial 3 minute denaturation at 94° C.; subsequent denaturation at 94° C. for 30 seconds; initial annealing temperature of 65° C. for 30 seconds; elongation at 68° C. for 30 seconds; second cycle annealing temperature of 63° C. for 30 seconds; all subsequent cycles, annealing temperature of 60° C. for a total of 35 cycles.

PCR products were then subjected to electrophoresis through a 3% agarose (BRL) gel using 1×TBE buffer, for 30 min at 200V. Gel images were documented using an Alpha Innotech 950® imaging system.

(B) Experimental Results (i) Identification of Differentially-expressed Genes between the SHR-SP, SHR and WKY by GeneCalling GeneCalling® reactions were performed on whole organs from adipose, kidney, heart, brain and liver as previously described, and gene expression profiles were compared between the SHR-SP and SHR and between the SHR and WKY animals.

An average of 20,000 GeneCalling® fragments were measured for relative abundance, yielding between 0.3% and 1.4% differences in gene expression. The results of this analysis are shown in Table 1. The SHR vs. WKY comparisons gave about 3-fold more differences than the SHR-SP vs. SHR comparisons, which is not surprising since the SHR-SP diverged from the SHR more recently than the SHR diverged from the WKY. By percentage, the most changes in gene expression were seen in the liver of the SHR relative to the WKY (1.4%), whereas the fewest changes were seen in the heart of the SHR-SP relative to the SHR (0.3%).

On average, three GeneCalling® fragments per gene were measured for relative abundance, allowing fault-tolerance in the event of sequence variation between the strains being compared. The relative abundance of each GeneCalling® fragment is illustrated in FIG. 1. Modulation was reported in fold-increase or fold-decrease in each tissue measured, with positive modulation (fold-increase) indicating increased MRNA abundance in the SHR (Table 2) or SHR-SP (Table 3) GeneCallinge samples.

Figures 2E, 2F:
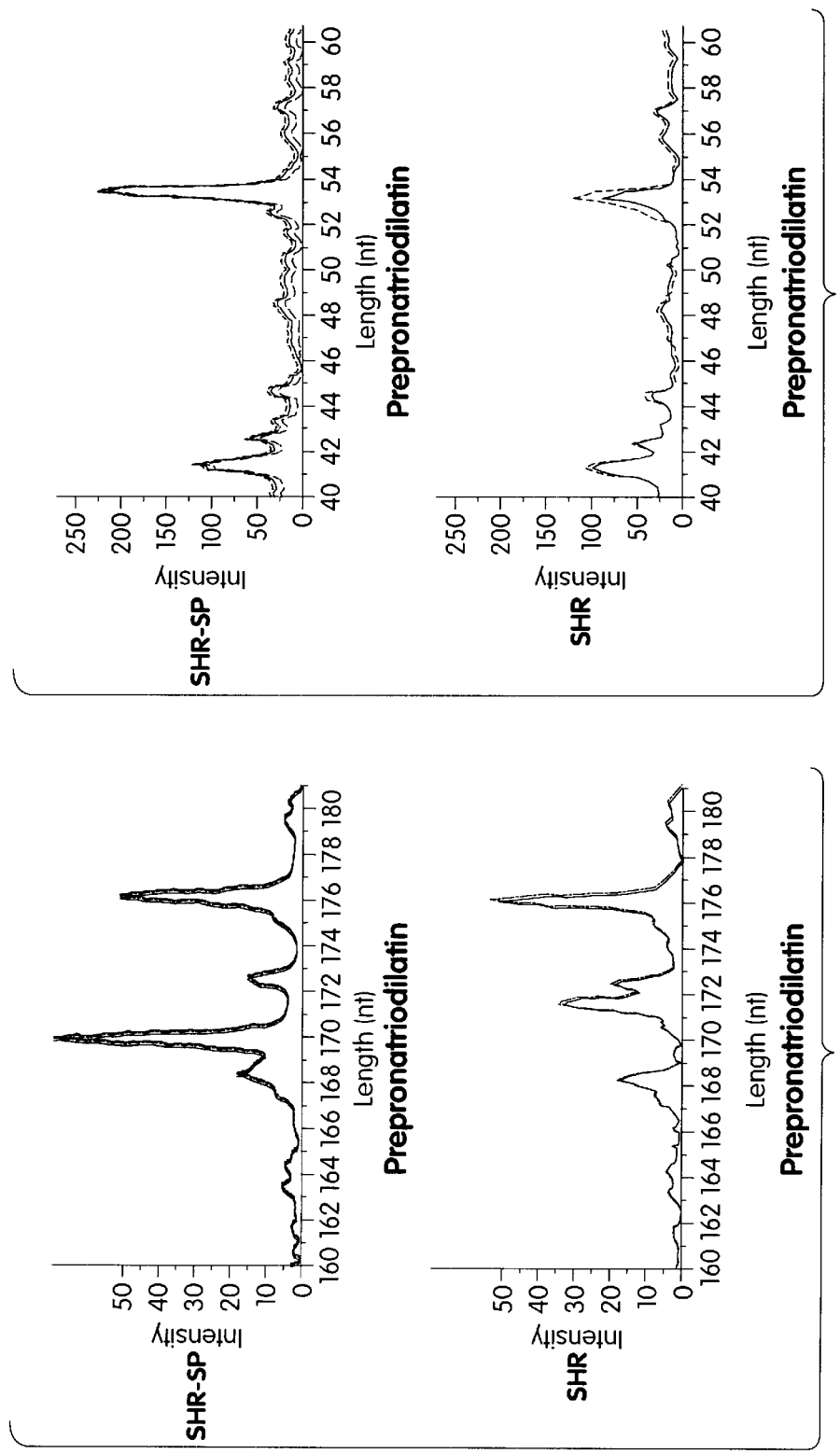
FIG. 2: Illustrates the differential-expression of selected genes. Data indicating differential expression of selected genes between the different genotypes is presented. In panel E, the GeneCalling® reaction identified a two base-pair deletion in the untranslated region of prepronatriodilatin which accounts for the shift of the peak from 172 to 170. The red vertical line indicates the peak of the expression difference. Fragment length in nucleotides is indicated on the x-axis, relative peak intensity is indicated on the y-axis. Each trace represents the composite of multiple reactions from a single animal.

Comparison of the SHR and WKY samples, resulted in the finding of a total of 48 differentially-expressed genes with identity or significant similarity to sequences which had been previously reported to GenBank. This figure accounted for approximately one-half the total number of gene expression differences (Table 2, FIG. 2). Interestingly, two genes were found to be modulated within all 5 tissues studied, indicating organism-wide alterations in gene expression which may link the phenotypes seen in the different organs.

Comparison of the SHR-SP and SHR samples, resulted in the finding of 14 differentially-expressed genes with significant similarity to sequences which had been previously reported to GenBank (Table 3, FIG. 2), with an average of 2.7 fragments per gene and one gene modulated across all 5 tissues.

(ii) Mapping of Differentially-Expressed Genes

Figures 3A, 3B:
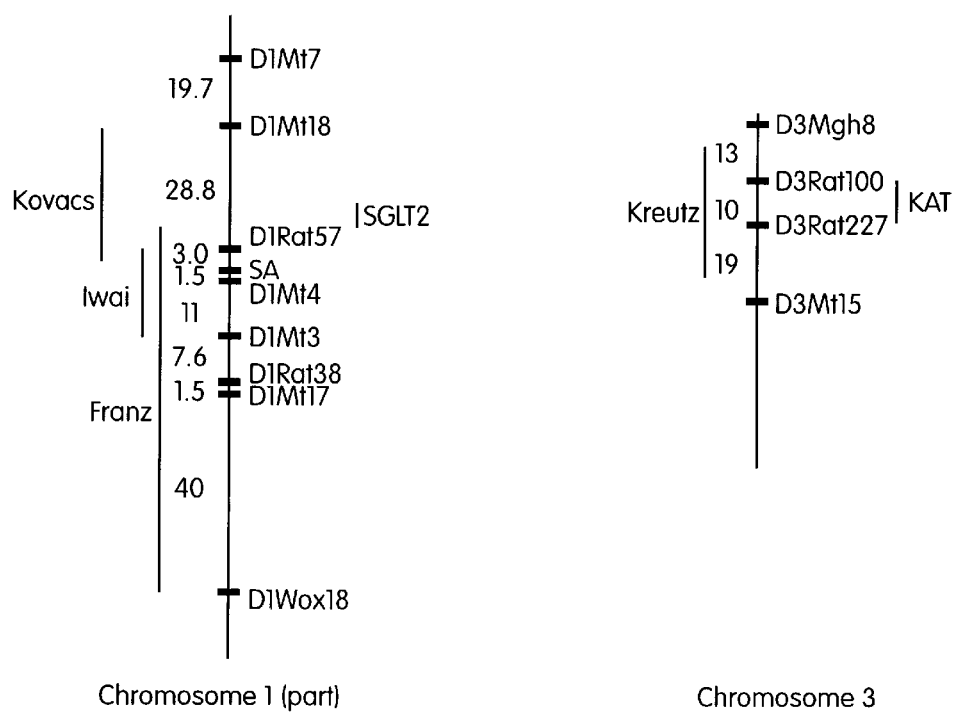
FIG. 3: Illustrates the mapping of differentially-expressed candidate genes. Examples of mapping data of differentially-expressed genes are shown and the LOD score is indicated below each gene name. The vertical bar to the right of the map indicates the 95% confidence interval in which the gene lies.

Differentially-expressed and previously unmapped genes of interest were placed on the physical map utilizing a radiation hybrid panel. Upon genotyping, map positions were constructed using RHMAPPER® computer program. Examples of mapped genes are shown in FIG. 3, Table 2, column 7 and Table 3, column 4. The map locations of the differentially-expressed genes were compared to quantitative trait loci (QTL) previously-reported in the literature and/or reported to GenBank. Of the 26 differentially-expressed genes whose map locations have been determined, six of the aforementioned genes mapped to within previously described QTL (FIG. 3, Table 1, Table 2). These six genes, in toto, as utilized within the scope of the present invention, were designated the GENE SET genes.

Specifically, the six differentially-expressed genes were mapped to the following chromosomal positions: (i) kynurenine aminotransferase mapped to chromosome 3 between D3rat100 and D3kyo2; (ii) CD36 mapped to chromosome 4 between D4rat5 and D4rat7; (iii) SGLT2 maps near the SA locus on chromosome 1; (iv) aldolase A maps near the SA locus on chromosome 1 and (v) both α cardiac myosin and α-tubulin are part of the RT complex on chromosome 20. In addition, the atrial natriuretic peptide (ANP) was found to map between Elaii1 and D5mgh16.

(iii) Detection of Mutated Genes Within the OTL

Sequence variations between the SHR-SP, SHR and WKY rodent strains were detected by direct sequencing of cDNAs which derived from PCR-amplified cDNA initially synthesized from oligo(dT)-selected, Poly (A)$^+$ RNA from the tissues analyzed for gene expression.

Amino acid substitutions were found in five of the six genes which were demonstrated to be differentially-expressed between the disease animal strains (i.e., SHR and SHP-SP) and the control strain (WKY) and which additionally mapped to QTL identified as contributing to the traits of interest in cross between the disease model and control.

Specifically, a conserved leucine (Leu) was found to be changed to glutamine (Glu) in the low-affinity, Na$^+$-dependent glucose transporter SGLT2 (L638Q) which was found to map within a region which has been previously shown to contain a gene(s) contributing to blood pressure variation (FIG. 3). The amino acid sequence of the region possessing the amino acid substitution of the SGLT2 variant (L638Q) in SHR, WKY, human, rabbit and pig is shown in FIG. 4 (SEQ ID NOS:1 and 9–12).

Kynurenine aminotransferase was demonstrated to possess an amino acid substitution which involves the changing of a specific charge at amino acid residue position 27 (E27G). Previously, this residue was found to be conserved across all known family members to the C. elegans kynurenine aminotransferase homolog, and the mutated gene also mapped to a region shown to be involved in blood pressure regulation. The amino acid sequence of the region possessing the amino acid substitution of the kynurenine aminotransferase variant (E27G) in SHR, WKY, human and nematode is shown in FIG. 4 (SEQ ID NOS:2 and 13–15).

Similarly, the fatty acid transport protein (FAT)/CD36 homolog was found to contain numerous amino acid substitutions and mapped to a region which was shown to be defective in the SHR, with regards to both glucose uptake and impaired fatty acid secretion.

The amino acid sequence of the region possessing the amino acid substitution in amino acid residues 148–191 (SEQ ID NO:3 and SEQ ID NOS:16–18) and amino acid residues 213–257 (SEQ ED NO:4 and SEQ ID NOS:19–21) of the FAT/CD36 variant in SHR-SP, SHR, WKY and mouse, respectively, is shown in FIG. 4.

Aldolase A was demonstrated to map to the stroke predisposition locus on chromosome 1 and possessed a methionine (Met) to valine (Val) amino acid substitution near the protein's amino terminus. It should be noted that the amino acid sequence of aldolase A is extremely conserved throughout numerous genus and species. The amino acid sequence of the region possessing the amino acid substitution of the aldolase A variant in SHR-SP, SHR, WKY, mouse, human, seal, dog and rabbit is shown in FIG. 4 (SEQ ID NOS:5 and 22–28).

The prepronatriodilatin gene, which encodes the atrial natriuretic peptide (ANP) was found to contain an altered glycine (Gly) amino acid residue in the SHR which is conserved across species, and mapped to a region which has been implicated in the etiology of both stroke and hypertension. See e.g., Rubattu, et al., 1996. Nat. Genet. 13(4):429–434. The amino acid sequence of the region possessing the amino acid substitution of the prepronatriodilatin variant in SHR-SP, SHR, WKY, human, pig and horse is shown in FIG. 4 (SEQ ID NOS:6 and 29–33).

Similarly, the amino acid sequence of the region possessing the amino acid substitution of the α-cardiac myosin variant in SHR-SP, SHR, WKY, mouse and human is shown in FIG. 4 (SEQ ID NOS:7 and 34–37) and the amino acid sequence of the region possessing the amino acid substitution of the α-tubulin variant in SHR, WKY, mouse, chicken, human and fluke is shown in FIG. 4 (SEQ ID NOS:8 and 38–42).

(C) Physiological and Biochemical Significance of the Experimental Results

Presented herein is the first comprehensive organ survey of differential gene expression in a genetic disease animal model, coupled with a comprehensive mapping and mutation-detection strategy to facilitate the identification of the specific gene(s) involved directly and/or indirectly in complex disease phenotypes The present invention, for the first time, implicates many new genes and their respective pathways in the mechanisms of these complex diseases, and highlights those genes whose variants may directly cause the disease phenotypes. Using this strategy to define the overlap between differential gene expression in a disease versus normal model and the map location(s) of the disease trait(s) is a powerful way of rapidly identifying genes that cause disease.

A total of sixty known rat genes (or rat homologs of genes known in other species) were found to be differentially-expressed in the analysis of five tissues. Six of these genes mapped to within chromosomal regions which have been implicated in various disease traits, and a total of seven genes were shown to possess amino acid substitutions which may influence these aforementioned disease traits.

(i) Hypertension- and Obesity-Related Genes

The differential-expression and amino acid substitution of the L638Q variant of the low affinity sodium-dependent glucose transporter, SGLT2, suggests that this transporter may be directly involved in the SHR phenotype. Activating mutations affecting selectivity, stoichiometry or activation state may increase sodium reabsorption, leading to plasma volume expansion and concomitant hypertension. Similarly, increased glucose reabsorption through this transporter enzyme, might lead to increased plasma glucose. Accordingly, antagonists/blockers of sodium-glucose transporter activity are currently being developed for utilization in anti-diabetic applications. See e.g., Tsujihara, al., 1996. *Chem. Pharm. Bull.* (Tokyo) 44(6):1174–1180.

The identification of kynurenine aminotransferase variant E27G, may help explain the previous finding that the activity of this enzyme in the SHR brain is greatly reduced relative to activity in the WKY brain. See e.g., Kapoor, et al., 1994. *Clin. Exp. Pharmacol. Physiol* 21(11):891–896. Kynurenine aminotransferase catalyzes the conversion of kynurenine to kynurenic acid, an excitatory amino acid receptor antagonist. This implicates the kynurenine pathway in blood pressure regulation and suggests the possibility that kynurenic acid may have anti-hypertensive applications. An associated increase in the expression of the water channel protein, aquaporin 3, suggests that increased water reabsorption, leading to plasma volume expansion, may be linked to anomalies in the kynurenine pathway. While aquaporin 2 is differentially-expressed in a congestive heart failure model (see e.g., Nielson, 1997. *Proc. Natl. Acad. Sci. USA* 94(10):5450–5455), aquaporin 3 is a thirst-responsive channel with a role in osmotically-driven water absorption across the collecting duct epithelium, which has no previous association with a disease state (see e.g., Ecelbarger, et al., 1995. *Am. J. Physiol.* 269(5):F663–672.

Increased expression of 21-hydroxylase, the final enzyme in aldosterone synthesis which is mutated in patients with adrenal hyperplasia (see e.g., Jospe, et al., 1987. *Biochem. Biophys. Res. Commun.* 142(3):798–804), putatively suggests a transcriptionally-regulated mechanism of increased aldosterone production. Interestingly, 21-hydroxylase alteration has also recently been associated with obesity/dyslipidemia (see e.g., Cornean, et al., 1998. *Arch. Dis. Child.* 78(3U:261–263), which may help to link these two features (i.e., obesity and hypertension) of human Metabolic Syndrome X.

(ii) Insulin Resistance-Related Genes

The tissue-wide decrease in the differential-expression of α-SNAP suggests an additional mechanism of insulin resistance in the SHR. Due to the fact that α-SNAP plays a key role in the translocation of the insulin-responsive glucose transporter GLUT4 to the cell surface (see e.g., Mastick, et al.,, 1997. *Endocrinology* 138(6):2391–2397), a significant decrease in the levels of the α-SNAP protein may lead to insulin resistance through a defective protein-trafficking or translocation mechanism.

The finding of numerous amino acid substitutions and coincident map location of the rat homologs of the fatty acid transport protein (FAT)/CD36, platelet glycoprotein IV and the class B scavenger receptor to a major locus of impaired fatty acid secretion, strongly suggests that this multi-functional transporter may be directly involved in glucose uptake and fatty acid secretion. Previously, this chromosome 4 locus was also demonstrated to be the only genetic determinant of impaired isoproterenol-mediated, non-esterified fatty acid secretion in the SHR (see e.g., Aitman, et al., 1997. *Nat. Genet.* 16(2):856–862). In addition, FAT/CD36 has been shown to bind and internalize oxidized, low density lipoprotein, bind thrombospondin and collagen 1, and when mutated in humans leads to a defect in platelet-collagen adhesion (see e.g., Frieda, et al., 1995. *J. Biol. Chem.* 270(7):2981–2986; Rigotti, et al., 1995. *J. Biol. Chem.* 270(27):16221–16224; Ibrahimi, et al., 1996. *Proc. Natl. Acad. Sci. U S A* 93(7):2646–2651). The association between the SHR CD36 allele and insulin resistance suggests further functionality of this receptor, and the finding of linkage of NIDDM to a potentially syntenic region of human 7q suggests that CD36 may play a causal role in insulin resistance in humans. Coincidentally, the SHR-SP version of CD36 differs from the SHR version and maps near the chromosome 4 stroke protective locus (see e.g., Rubattu, et al., 1996. *Nat. Genet.* 13(4):429–434), suggesting the possibility of its involvement in the stroke phenotype as well.

Increased expression of the cardiac isoform of fatty acid binding protein (FABP) in the SHR adipocytes suggests a role for this member the FABP family in insulin resistance. Variants in the intestinal and adipocyte FABPs have been linked to obesity, dyslipidemia and insulin resistance (see e.g., Hotamisligil, et al., 1996. *Science* 274:1377–1379; Baier, et al., 1995. *J. Clin. Invest.* 95(3):1281–1287). While the cDNA sequence of this gene was identical in the SHR and WKY rats, the differing levels of mRNA detected may affect protein levels contributing to the phenotype.

(iii) Stroke Predisposition-Related Genes

The discovery of the differential expression of a novel variant of prepronatriodilatin, which was mapped to a region associated with an increased stroke latency period (see e.g., Rubattu, et al., 1996. *Nat. Genet.* 13(4):429–434) and with increased infarct volume (see e.g., Jeffs, et al., 1997. *Nat. Genet.* 16(4):364–367), suggests a novel, blood pressure-independent role in stroke predisposition for the peptide hormones encoded by this gene. The fact that the products of this gene circulate in the bloodstream and may serve a protective role in stroke, serves to facilitate the development of pharmaceutical compounds for utilization in therapeutic intervention of stroke.

The finding of differential expression and amino acid substitution in the extremely conserved aldolase A gene, as well as its coincident location near a region of stroke predisposition, suggests that this enzyme (whose activity has long been known to be elevated in the sera of patients with cerebrovascular insult) may play a direct role in the onset of the cerebrovascular event. The amino acid residue which is substituted in the SHR-SP has been demonstrated to be completely conserved in every organisms from which it has been sequenced, including at least 12 mammals. While aldolase A is a well-characterized, glucose-induced glycolytic enzyme, it has been shown to bind a-tubulin, whose MRNA accumulates after transient ischemic brain insult (see e.g., Volker & Knull, 1997. *Arch. Biochem. Biophys.* 338 (2):237–243). Breakdown of the cytoskeleton has been proposed to be a central event in the evolution of ischemic brain damage. In addition, an amino acid substitution (S340T) was found in α-tubulin in the SHR and SHR-SP, relative to the amino acid sequence of the protein in both WKY control rodents and literature-reported sequences. This evidence suggests the possible involvement of aldolase A and a-tubulin in predisposition to vascular injury.

In addition, the demonstration of increased expression of cystatin C in the SHR-SP brain may play a significant role in the stroke phenotype, as mutations of this cysteine protease inhibitor, in humans, has been shown to cause cerebral hemmhorage (see e.g., Ghiso, et al., 1986. *Proc. Natl. Acad. Sci. USA* 83(9):2974–2978). While the human mutation does not alter the ability of cystatin C to inhibit cathepsin B, it does, nonetheless, permit dimerization and aggregation which leads to its subsequent deposition as amyloid. In the SHR-SP model, increased cystatin C synthesis may have an equally physiologically-deleterious effect on the cerebrovasculature by an accumulation of protein leading to aggregation.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publication are cited herein, the disclosures of which are incorporated by reference in their entireties.

---

What is claimed is:

1. An isolated variant CD36 polypeptide, wherein said variant CD36 polypeptide consists of the amino acid sequence of SEQ ID NO:44 substituted at amino acid positions 213–257 by the amino acid sequence of SEQ ID NO:19.

2. An isolated variant CD36 polypeptide, wherein said variant CD36 polypeptide consists of the amino acid sequence of SEQ ID NO:44 substituted at amino acid positions 148–191 by the amino acid sequence of SEQ ID NO:16.

3. An isolated variant CD36 polypeptide, wherein said variant CD36 polypeptide consists of the amino acid sequence of SEQ ID NO:44 substituted at amino acid positions 213–257 by the amino acid sequence of SEQ ID NO:19 and substituted at amino acid positions 148–191 by the amino acid sequence of SEQ ID NO:16.

* * * * *

SEQUENCE LISTING

```
<160> NUMBER OF SEQ ID NOS: 44

<210> SEQ ID NO 1
<211> LENGTH: 20
<212> TYPE: PRT
<213> ORGANISM: Rattus sp.

<400> SEQUENCE: 1

Glu Glu Val Ala Ala Thr Thr Arg Arg Gln Glu Asp Ile Ser Glu Asp
 1               5                  10                  15

Pro Ser Trp Ala
            20

<210> SEQ ID NO 2
<211> LENGTH: 19
<212> TYPE: PRT
<213> ORGANISM: Rattus sp.

<400> SEQUENCE: 2

Asn Leu Trp Val Glu Phe Gly Lys Leu Thr Lys Gly Tyr Asp Val Val
 1               5                  10                  15

Asn Leu Gly

<210> SEQ ID NO 3
<211> LENGTH: 44
<212> TYPE: PRT
<213> ORGANISM: Rattus sp.

<400> SEQUENCE: 3

Tyr Thr Asn Ser Phe Val Gln Gly Val Leu Asn Ser Leu Ile Lys Lys
 1               5                  10                  15

Ser Lys Ser Ser Met Phe Gln Thr Arg Ser Leu Lys Glu Leu Leu Trp
            20                  25                  30

Gly Tyr Lys Asp Pro Phe Leu Ser Leu Val Pro Tyr
        35                  40

<210> SEQ ID NO 4
<211> LENGTH: 45
<212> TYPE: PRT
<213> ORGANISM: Rattus sp.

<400> SEQUENCE: 4

Val Phe Asn Gly Lys Asp Asn Ile Ser Lys Val Ala Ile Ile Asp Thr
```

-continued

```
                1               5                  10                 15
Tyr Lys Gly Lys Arg Asn Leu Ser Tyr Trp Lys Ser Tyr Cys Asp Met
                        20                  25                  30

Ile Asn Gly Thr Asp Ala Ala Ser Phe Pro Pro Phe Gly
            35                  40                  45

<210> SEQ ID NO 5
<211> LENGTH: 20
<212> TYPE: PRT
<213> ORGANISM: Rattus sp.

<400> SEQUENCE: 5

Gly Glu His Thr Pro Ser Ser Leu Ala Ile Val Glu Asn Ala Asn Val
 1               5                  10                  15

Leu Ala Arg Tyr
            20

<210> SEQ ID NO 6
<211> LENGTH: 23
<212> TYPE: PRT
<213> ORGANISM: Rattus sp.

<400> SEQUENCE: 6

Ser Gln Arg Asp Gly Gly Ala Leu Gly Arg Ser Pro Trp Asp Pro Ser
 1               5                  10                  15

Asp Arg Ser Ala Leu Leu Lys
            20

<210> SEQ ID NO 7
<211> LENGTH: 37
<212> TYPE: PRT
<213> ORGANISM: Rattus sp.

<400> SEQUENCE: 7

Ala Leu Gln Glu Ala His Gln Gln Ala Leu Asp Asp Leu Gln Ala Glu
 1               5                  10                  15

Glu Asp Lys Val Asn Thr Leu Ile Lys Ser Lys Val Lys Leu Glu Gln
            20                  25                  30

Gln Val Asp Asp Leu
            35

<210> SEQ ID NO 8
<211> LENGTH: 50
<212> TYPE: PRT
<213> ORGANISM: Rattus sp.

<400> SEQUENCE: 8

Ala Cys Cys Leu Leu Tyr Arg Gly Asp Val Val Pro Lys Asp Val Asn
 1               5                  10                  15

Ala Ala Ile Ala Thr Ile Lys Thr Lys Arg Ser Ile Gln Phe Val Asp
            20                  25                  30

Trp Cys Pro Thr Gly Phe Lys Val Gly Ile Asn Tyr Gln Pro Pro Thr
            35                  40                  45

Val Val
    50

<210> SEQ ID NO 9
<211> LENGTH: 20
<212> TYPE: PRT
<213> ORGANISM: Rattus sp.
```

-continued

```
<400> SEQUENCE: 9

Glu Glu Val Ala Ala Thr Thr Arg Arg Leu Glu Asp Ile Ser Glu Asp
  1               5                  10                  15

Pro Ser Trp Ala
            20

<210> SEQ ID NO 10
<211> LENGTH: 20
<212> TYPE: PRT
<213> ORGANISM: Homo sapiens

<400> SEQUENCE: 10

Glu Glu Ala Ala Ala Ala Ala Arg Arg Leu Glu Asp Ile Ser Glu Asp
  1               5                  10                  15

Pro Ser Trp Ala
            20

<210> SEQ ID NO 11
<211> LENGTH: 20
<212> TYPE: PRT
<213> ORGANISM: Oryctolagus cuniculus

<400> SEQUENCE: 11

Glu Glu Glu Ala Ala Ala Ala Arg Arg Leu Glu Asp Ile Asn Glu Asp
  1               5                  10                  15

Pro Arg Trp Ser
            20

<210> SEQ ID NO 12
<211> LENGTH: 20
<212> TYPE: PRT
<213> ORGANISM: Sus sp.

<400> SEQUENCE: 12

Glu Glu Glu Glu Ala Gln Lys Arg Lys Leu Thr Asp Thr Ser Glu Lys
  1               5                  10                  15

Pro Leu Trp Lys
            20

<210> SEQ ID NO 13
<211> LENGTH: 19
<212> TYPE: PRT
<213> ORGANISM: Rattus sp.

<400> SEQUENCE: 13

Asn Leu Trp Val Glu Phe Gly Lys Leu Thr Lys Glu Tyr Asp Val Val
  1               5                  10                  15

Asn Leu Gly

<210> SEQ ID NO 14
<211> LENGTH: 19
<212> TYPE: PRT
<213> ORGANISM: Homo sapiens

<400> SEQUENCE: 14

Asn Pro Trp Val Glu Phe Val Lys Leu Ala Ser Glu His Asp Val Val
  1               5                  10                  15

Asn Leu Gly

<210> SEQ ID NO 15
<211> LENGTH: 19
```

```
<212> TYPE: PRT
<213> ORGANISM: Caenorhabditis sp.

<400> SEQUENCE: 15

Ser Ile Trp Val Glu Phe Thr Thr Leu Ala Ala Glu Thr Lys Ala Val
 1               5                  10                  15

Asn Leu Gly

<210> SEQ ID NO 16
<211> LENGTH: 44
<212> TYPE: PRT
<213> ORGANISM: Rattus sp.

<400> SEQUENCE: 16

Tyr Gln Asn Ser Phe Phe Gln Gly Val Leu Asn Ile Phe Ile Lys Lys
 1               5                  10                  15

Ser Lys Ser Ser Met Phe Gln Thr Arg Ser Leu Lys Glu Leu Leu Trp
            20                  25                  30

Gly Tyr Glu Asp Pro Phe Leu Ser Leu Ile Pro Tyr
        35                  40

<210> SEQ ID NO 17
<211> LENGTH: 44
<212> TYPE: PRT
<213> ORGANISM: Rattus sp.

<400> SEQUENCE: 17

Tyr Thr Asn Ser Phe Val Gln Gly Val Leu Asn Ser Leu Ile Lys Lys
 1               5                  10                  15

Ser Lys Ser Ser Met Phe Gln Thr Arg Ser Leu Lys Glu Leu Leu Trp
            20                  25                  30

Gly Tyr Lys Asp Pro Phe Leu Ser Leu Val Pro Tyr
        35                  40

<210> SEQ ID NO 18
<211> LENGTH: 44
<212> TYPE: PRT
<213> ORGANISM: Mus sp.

<400> SEQUENCE: 18

Tyr Gln Asn Ser Phe Val Gln Val Val Leu Asn Ser Leu Ile Lys Lys
 1               5                  10                  15

Ser Lys Ser Ser Met Phe Gln Thr Arg Ser Leu Lys Glu Leu Leu Trp
            20                  25                  30

Gly Tyr Lys Asp Pro Phe Leu Ser Leu Val Pro Tyr
        35                  40

<210> SEQ ID NO 19
<211> LENGTH: 45
<212> TYPE: PRT
<213> ORGANISM: Rattus sp.

<400> SEQUENCE: 19

Val Phe Asn Gly Lys Asp Asn Ile Ser Lys Val Ala Ile Ile Asp Thr
 1               5                  10                  15

Tyr Lys Gly Lys Arg Asn Leu Ser Tyr Trp Glu Ser Tyr Cys Asp Met
            20                  25                  30

Ile Asn Gly Thr Asp Ala Ala Ser Phe Pro Pro Leu Gly
        35                  40                  45
```

```
<210> SEQ ID NO 20
<211> LENGTH: 45
<212> TYPE: PRT
<213> ORGANISM: Rattus sp.

<400> SEQUENCE: 20

Val Ser Asn Gly Lys Asp Asn Ile Ser Lys Val Ala Ile Ile Asp Thr
 1               5                  10                  15

Tyr Lys Gly Lys Arg Asn Leu Ser Tyr Trp Lys Ser Tyr Cys Asp Met
                20                  25                  30

Ile Asn Gly Thr Asp Ala Ala Ser Phe Pro Pro Leu Gly
            35                  40              45

<210> SEQ ID NO 21
<211> LENGTH: 45
<212> TYPE: PRT
<213> ORGANISM: Mus sp.

<400> SEQUENCE: 21

Val Phe Asn Gly Lys Asp Asn Ile Ser Lys Val Ala Ile Ile Glu Ser
 1               5                  10                  15

Tyr Lys Gly Lys Arg Asn Leu Ser Tyr Trp Pro Ser Tyr Cys Asp Met
                20                  25                  30

Ile Asn Gly Thr Asp Ala Ala Ser Phe Pro Pro Phe Val
            35                  40              45

<210> SEQ ID NO 22
<211> LENGTH: 20
<212> TYPE: PRT
<213> ORGANISM: Rattus sp.

<400> SEQUENCE: 22

Gly Glu His Thr Pro Ser Ser Leu Ala Ile Met Glu Asn Ala Asn Val
 1               5                  10                  15

Leu Ala Arg Tyr
            20

<210> SEQ ID NO 23
<211> LENGTH: 20
<212> TYPE: PRT
<213> ORGANISM: Rattus sp.

<400> SEQUENCE: 23

Gly Glu His Thr Pro Ser Ser Leu Ala Ile Met Glu Asn Ala Asn Val
 1               5                  10                  15

Leu Ala Arg Tyr
            20

<210> SEQ ID NO 24
<211> LENGTH: 20
<212> TYPE: PRT
<213> ORGANISM: Mus sp.

<400> SEQUENCE: 24

Gly Glu His Thr Pro Ser Ala Leu Ala Ile Met Glu Asn Ala Asn Val
 1               5                  10                  15

Leu Ala Arg Tyr
            20

<210> SEQ ID NO 25
<211> LENGTH: 20
<212> TYPE: PRT
```

```
<213> ORGANISM: Homo sapiens

<400> SEQUENCE: 25

Gly Glu His Thr Pro Ser Ala Leu Ala Ile Met Glu Asn Ala Asn Val
 1               5                  10                  15

Leu Ala Arg Tyr
            20

<210> SEQ ID NO 26
<211> LENGTH: 20
<212> TYPE: PRT
<213> ORGANISM: Unknown
<220> FEATURE:
<223> OTHER INFORMATION: Description of Unknown Organism: Seal

<400> SEQUENCE: 26

Gly Glu His Thr Pro Ser Ala Leu Ala Ile Met Glu Asn Ala Asn Val
 1               5                  10                  15

Leu Ala Arg Tyr
            20

<210> SEQ ID NO 27
<211> LENGTH: 20
<212> TYPE: PRT
<213> ORGANISM: Canis familiaris

<400> SEQUENCE: 27

Gly Glu His Thr Pro Ser Ala Leu Ala Ile Met Glu Asn Ala Asn Val
 1               5                  10                  15

Leu Ala Arg Tyr
            20

<210> SEQ ID NO 28
<211> LENGTH: 20
<212> TYPE: PRT
<213> ORGANISM: Oryctolagus cuniculus

<400> SEQUENCE: 28

Gly Glu His Thr Pro Ser Ala Leu Ala Ile Met Glu Asn Ala Asn Val
 1               5                  10                  15

Leu Ala Arg Tyr
            20

<210> SEQ ID NO 29
<211> LENGTH: 23
<212> TYPE: PRT
<213> ORGANISM: Rattus sp.

<400> SEQUENCE: 29

Ser Gln Arg Asp Gly Gly Ala Leu Gly Arg Gly Pro Trp Asp Pro Ser
 1               5                  10                  15

Asp Arg Ser Ala Leu Leu Lys
            20

<210> SEQ ID NO 30
<211> LENGTH: 23
<212> TYPE: PRT
<213> ORGANISM: Rattus sp.

<400> SEQUENCE: 30

Ser Gln Arg Asp Gly Gly Ala Leu Gly Arg Ser Pro Trp Asp Pro Ser
 1               5                  10                  15
```

Asp Arg Ser Ala Leu Leu Lys
            20

<210> SEQ ID NO 31
<211> LENGTH: 23
<212> TYPE: PRT
<213> ORGANISM: Homo sapiens

<400> SEQUENCE: 31

Ala Gln Arg Asp Gly Gly Ala Leu Gly Arg Gly Pro Trp Asp Ser Ser
  1               5                  10                  15

Asp Arg Ser Ala Leu Leu Lys
            20

<210> SEQ ID NO 32
<211> LENGTH: 23
<212> TYPE: PRT
<213> ORGANISM: Sus sp.

<400> SEQUENCE: 32

Ala Gln Arg Asp Gly Gly Ala Leu Gly Arg Gly Pro Trp Asp Ala Ser
  1               5                  10                  15

Asp Arg Ser Ala Leu Leu Lys
            20

<210> SEQ ID NO 33
<211> LENGTH: 23
<212> TYPE: PRT
<213> ORGANISM: Equus caballus

<400> SEQUENCE: 33

Ala Gln Arg Asp Gly Gly Ala Leu Gly Arg Gly Ser Trp Asp Ser Ser
  1               5                  10                  15

Asp Arg Ser Ala Leu Leu Lys
            20

<210> SEQ ID NO 34
<211> LENGTH: 37
<212> TYPE: PRT
<213> ORGANISM: Rattus sp.

<400> SEQUENCE: 34

Ala Leu Gln Glu Ala His Gln Gln Ala Leu Asp Asp Leu Gln Ala Glu
  1               5                  10                  15

Glu Asp Lys Val Asn Thr Leu Thr Lys Ser Lys Val Lys Leu Glu Gln
            20                  25                  30

Gln Val Asp Asp Leu
        35

<210> SEQ ID NO 35
<211> LENGTH: 37
<212> TYPE: PRT
<213> ORGANISM: Rattus sp.

<400> SEQUENCE: 35

Ala Leu Gln Glu Ala His Gln Gln Ala Leu Asp Asp Leu Gln Ala Glu
  1               5                  10                  15

Glu Asp Lys Val Asn Thr Leu Thr Lys Ser Lys Val Lys Leu Glu Gln
            20                  25                  30

Gln Val Asp Asp Leu
        35

```
<210> SEQ ID NO 36
<211> LENGTH: 37
<212> TYPE: PRT
<213> ORGANISM: Mus sp.

<400> SEQUENCE: 36

Ala Leu Gln Glu Ala His Gln Gln Ala Leu Asp Asp Leu Gln Ala Glu
 1               5                  10                  15

Glu Asp Lys Val Asn Thr Leu Thr Lys Ser Lys Val Lys Leu Glu Gln
            20                  25                  30

Gln Val Asp Asp Leu
        35

<210> SEQ ID NO 37
<211> LENGTH: 37
<212> TYPE: PRT
<213> ORGANISM: Homo sapiens

<400> SEQUENCE: 37

Ala Leu Gln Glu Ala His Gln Gln Ala Leu Asp Asp Leu Gln Ala Glu
 1               5                  10                  15

Glu Asp Lys Val Asn Thr Leu Thr Lys Ala Lys Val Lys Leu Glu Gln
            20                  25                  30

Gln Val Asp Asp Leu
        35

<210> SEQ ID NO 38
<211> LENGTH: 50
<212> TYPE: PRT
<213> ORGANISM: Rattus sp.

<400> SEQUENCE: 38

Ala Cys Cys Leu Leu Tyr Arg Gly Asp Val Val Pro Lys Asp Val Asn
 1               5                  10                  15

Ala Ala Ile Ala Thr Ile Lys Thr Lys Arg Thr Ile Gln Phe Val Asp
            20                  25                  30

Trp Cys Pro Thr Gly Phe Lys Val Gly Ile Asn Tyr Gln Pro Pro Thr
            35                  40                  45

Val Val
    50

<210> SEQ ID NO 39
<211> LENGTH: 50
<212> TYPE: PRT
<213> ORGANISM: Mus sp.

<400> SEQUENCE: 39

Ala Cys Cys Leu Leu Tyr Arg Gly Asp Val Val Pro Lys Asp Val Asn
 1               5                  10                  15

Ala Ala Ile Ala Thr Ile Lys Thr Lys Arg Thr Ile Gln Phe Val Asp
            20                  25                  30

Trp Cys Pro Thr Gly Phe Lys Val Gly Ile Asn Tyr Gln Pro Pro Thr
            35                  40                  45

Val Val
    50

<210> SEQ ID NO 40
<211> LENGTH: 50
<212> TYPE: PRT
<213> ORGANISM: Gallus sp.
```

<400> SEQUENCE: 40

Ala Cys Cys Leu Leu Tyr Arg Gly Asp Val Val Pro Lys Asp Val Asn
1               5                   10                  15

Ala Ala Ile Ala Thr Ile Lys Thr Lys Arg Thr Ile Gln Phe Val Asp
            20                  25                  30

Trp Cys Pro Thr Gly Phe Lys Val Gly Ile Asn Tyr Gln Pro Pro Thr
        35                  40                  45

Val Val
    50

<210> SEQ ID NO 41
<211> LENGTH: 50
<212> TYPE: PRT
<213> ORGANISM: Homo sapiens

<400> SEQUENCE: 41

Ala Cys Cys Met Leu Tyr Arg Gly Asp Val Val Pro Lys Asp Val Asn
1               5                   10                  15

Ala Ala Ile Ala Thr Ile Lys Thr Lys Arg Thr Ile Gln Phe Val Asp
            20                  25                  30

Trp Cys Pro Thr Gly Phe Lys Val Gly Ile Asn Tyr Gln Pro Pro Thr
        35                  40                  45

Val Val
    50

<210> SEQ ID NO 42
<211> LENGTH: 50
<212> TYPE: PRT
<213> ORGANISM: Unknown
<220> FEATURE:
<223> OTHER INFORMATION: Description of Unknown Organism: Fluke

<400> SEQUENCE: 42

Ala Cys Cys Met Leu Tyr Arg Gly Asp Val Val Pro Lys Asp Val Asn
1               5                   10                  15

Ala Ala Ile Ala Thr Ile Lys Thr Lys Arg Thr Ile Gln Phe Val Asp
            20                  25                  30

Trp Cys Pro Thr Gly Phe Lys Val Gly Ile Asn Tyr Gln Pro Pro Thr
        35                  40                  45

Val Val
    50

<210> SEQ ID NO 43
<211> LENGTH: 26
<212> TYPE: DNA
<213> ORGANISM: Artificial Sequence
<220> FEATURE:
<223> OTHER INFORMATION: Description of Artificial Sequence:
      oligo(dT)<25>V

<400> SEQUENCE: 43
tttttttttt tttttttttt tttttv                                        26

<210> SEQ ID NO 44
<211> LENGTH: 472
<212> TYPE: PRT
<213> ORGANISM: Rattus norvegicus

<400> SEQUENCE: 44

Met Gly Cys Asp Arg Asn Cys Gly Leu Ile Thr Gly Ala Val Ile Gly

-continued

```
  1               5                   10                  15
Ala Val Leu Ala Val Phe Gly Gly Ile Leu Met Pro Val Gly Asp Leu
                    20                  25                  30

Leu Ile Glu Lys Thr Ile Lys Arg Glu Val Val Leu Glu Glu Gly Thr
            35                  40                  45

Ile Ala Phe Lys Asn Trp Val Lys Thr Gly Thr Thr Val Tyr Arg Gln
        50                  55                  60

Phe Trp Val Phe Asp Val Gln Asn Pro Glu Glu Val Ala Lys Asn Ser
 65                     70                  75                  80

Ser Lys Ile Lys Val Ile Gln Arg Gly Pro Tyr Thr Tyr Arg Val Arg
                    85                  90                  95

Tyr Leu Ala Lys Glu Asn Ile Thr Gln Asp Pro Lys Asp Ser Thr Val
                100                 105                 110

Ser Phe Val Gln Pro Asn Gly Ala Ile Phe Glu Pro Ser Leu Ser Val
            115                 120                 125

Gly Thr Glu Asn Asp Asn Phe Thr Val Leu Asn Leu Ala Val Ala Ala
        130                 135                 140

Ala Pro His Ile Tyr Thr Asn Ser Phe Val Gln Gly Val Leu Asn Ser
145                 150                 155                 160

Leu Ile Lys Lys Ser Lys Ser Ser Met Phe Gln Thr Arg Ser Leu Lys
                    165                 170                 175

Glu Leu Leu Trp Gly Tyr Lys Asp Pro Phe Leu Ser Leu Val Pro Tyr
                180                 185                 190

Pro Ile Ser Thr Thr Val Gly Val Phe Tyr Pro Tyr Asn Asn Thr Val
            195                 200                 205

Asp Gly Val Tyr Lys Val Ser Asn Gly Lys Asp Asn Ile Ser Lys Val
        210                 215                 220

Ala Ile Ile Asp Thr Tyr Lys Gly Lys Arg Asn Leu Ser Tyr Trp Glu
225                 230                 235                 240

Ser Tyr Cys Asp Met Ile Asn Gly Thr Asp Ala Ala Ser Phe Pro Pro
                    245                 250                 255

Leu Gly Glu Lys Ser Arg Thr Leu Arg Phe Phe Ser Ser Asp Ile Cys
                260                 265                 270

Arg Ser Ile Tyr Ala Val Phe Glu Ser Glu Val Asn Leu Lys Gly Ile
            275                 280                 285

Pro Val Tyr Arg Phe Val Leu Pro Ala Asn Ala Phe Ala Ser Pro Leu
        290                 295                 300

Gln Asn Pro Asp Asn His Cys Phe Cys Thr Glu Lys Val Ile Ser Asn
305                 310                 315                 320

Asn Cys Thr Ser Tyr Gly Val Leu Asp Ile Gly Lys Cys Lys Glu Gly
                    325                 330                 335

Lys Pro Val Tyr Asn Ser Leu Pro His Phe Leu His Ala Ser Pro Asp
                340                 345                 350

Val Ser Glu Pro Ile Glu Gly Leu Asn Pro Thr Glu Asp Glu His Arg
            355                 360                 365

Thr Tyr Leu Asp Val Glu Pro Ile Thr Gly Phe Thr Leu Gln Phe Ser
        370                 375                 380

Lys Arg Leu Gln Val Asn Ile Leu Val Lys Pro Ala Arg Lys Ile Glu
385                 390                 395                 400

Ala Leu Lys Asn Leu Lys Arg Pro Tyr Ile Val Pro Ile Leu Trp Leu
                    405                 410                 415

Asn Glu Thr Gly Thr Ile Gly Asp Glu Lys Ala Glu Met Phe Arg Asn
                420                 425                 430
```

-continued

```
Gln Val Thr Gly Lys Ile Lys Leu Leu Gly Leu Val Glu Met Val Leu
        435                 440                 445
Leu Gly Val Gly Val Val Met Phe Val Ala Phe Met Ile Ser Tyr Cys
        450                 455                 460
Ala Cys Arg Ser Lys Asn Gly Lys
465                 470
```